US010265297B2

(12) United States Patent
Trivedi et al.

(10) Patent No.: US 10,265,297 B2
(45) Date of Patent: Apr. 23, 2019

(54) FORMULATION FOR THE PREVENTION AND TREATMENT OF BONE RELATED DISORDERS

(71) Applicant: Council of Scientific & Industrial Research, New Delhi (IN)

(72) Inventors: Ritu Trivedi, Uttar Pradesh (IN); Prabhat Ranjan Mishra, Uttar Pradesh (IN); Sulekha Adhikary, Uttar Pradesh (IN); Naseer Ahmad, Uttar Pradesh (IN); Dharmendra Choudhary, Uttar Pradesh (IN); Naresh Mittapelly, Uttar Pradesh (IN); Sudhir Kumar, Uttar Pradesh (IN); Kapil Dev, Uttar Pradesh (IN); Rakesh Maurya, Uttar Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/635,457

(22) Filed: Jun. 28, 2017

(65) Prior Publication Data

US 2018/0000776 A1   Jan. 4, 2018

(30) Foreign Application Priority Data

Jul. 1, 2016  (IN) .............................. 201611022640

(51) Int. Cl.
| | | |
|---|---|---|
| A61K 36/21 | (2006.01) | |
| A61K 31/357 | (2006.01) | |
| A61K 9/107 | (2006.01) | |
| A61K 9/00 | (2006.01) | |
| A61K 47/12 | (2006.01) | |
| A61K 47/26 | (2006.01) | |
| A61K 47/10 | (2017.01) | |
| A61K 9/08 | (2006.01) | |

(52) U.S. Cl.
CPC .......... *A61K 31/357* (2013.01); *A61K 9/0019* (2013.01); *A61K 9/0053* (2013.01); *A61K 9/0095* (2013.01); *A61K 9/08* (2013.01); *A61K 9/107* (2013.01); *A61K 36/21* (2013.01); *A61K 47/10* (2013.01); *A61K 47/12* (2013.01); *A61K 47/26* (2013.01); *A61K 2236/15* (2013.01); *A61K 2236/33* (2013.01); *A61K 2236/39* (2013.01)

(58) Field of Classification Search
None
See application file for complete search history.

(56) References Cited

PUBLICATIONS

Edenharder, R. et al. Isolation and Characterization of Structurally Novel Antimutagenic Flavonoids from Spinach. J Agric Food Chem 49:2767-2773, 2001. (Year: 2001).*
Bergquist S. et al. Flavonoids in Baby Spinach. J Agric Food Chem 53:9459-9464, 2005. (Year: 2005).*
Aritomi, M. et al. Chemical Studies on the Edible Plants, Part 5. Phytochemistry 25(1)231-4, 1986. (Year: 1986).*
Oettmeier W. et al. Identification of Flavonoids and Cinnamic Acid Derivatives from Spinach Chloroplast Preparations. Zeitschrift fuer Naturforschung, Teil B. 27(2)177-183, 1972. (Year: 1972).*
Kumar M. et al. Antiosteoporotic Constituents from Indian Medicinal Plants. Phytomedicine 17(13)993-999, 2010. (Year: 2010).*
Berg, S. et al. Systematicf Review of Herbals as Potential Antiinflammatory Agents. Pharmacognosy Reviews 5(1)120-137, Jul. 2011. (Year: 2011).*
Jain et al., Hepatoprotective activity of *Chenopodium album* Linn: in vitro and in vivo studies, Journal of Experimental and Integrative Medicine 2012: 2(4):331-336.
Chu et al., Antioxidant and Antiproliferative Activities of Common Vegetables, Journal of Agricultural and Food Chemistry, 2002, 50, 6910-6916.
Bickford et al, Antioxidant-rich diets improve cerebellar physiology and motor learning in aged rats, Brain Research 2000, 866, 211-217.
Gil et al, Effect of Postharvest Storage and Processing on the Antioxidant Constituents (Flavonoids and Vitamin C) of Fresh Cut Spincach, J. Agric. Food Chem., 1999, 47, 2213-2217.
Bergquist et al., Flavonoids in Baby Spinach (Spinacia oleracea L.): Changes during Plant Growth and Storage, Journal of Agricultural and Food Chemistry, 2005, 53, 9459-9464.
Gomathi et al., Antidiabetic activity of leaves of *Spinacia oleracea* Linn. In Alloxan-induced diabetic rats, Journal of Chemical and Pharmaceutical Research, 2010, 2(4): 266-274.
Al-Dosari, S. Mohammed, Antioxidant and Protective Effects of Spincach (*Spinacia oleraccea* L.) Leaves Against Carbon Tetrachloride-Induced Liver Injury, Clinical and Experimental Medical Journal 2010, vol. 4, No. 1, 129-140.
Sultana et al., Flavonols (kaempeferol, quercetin, myricetin) contents of selected fruits, vegetables and medicinal plants, Food Chemistry, 2008, 108, 879-884.

(Continued)

*Primary Examiner* — Ralph J Gitomer
(74) *Attorney, Agent, or Firm* — Blank Rome LLP

(57) ABSTRACT

The present invention relates to a formulation of *Spinacea oleracea* useful for the prevention or treatment of osteohealth related disorders. The present invention relates to the field of pharmaceutical formulation that provides extract, fractions, pure compound isolated from natural sources and formulation thereof useful for the prevention and treatment of various medical indications. Further, this invention relates to conditions associated with estrogen dependent or independent diseases (primary/secondary osteoporosis) or syndromes or disorders preferably relating to cartilage such as osteoarthritis caused in humans and animals. Furthermore, this invention relates to achievement of peak bone mass during skeletal growth and health in humans and animals. Particularly, the present invention relates to the processes for the preparation of biologically active extracts, from *Spinacea oleracea* from the family Amaranthaceae their pharmaceutically acceptable excepients and compositions of the principal aspect of the present invention.

21 Claims, 8 Drawing Sheets

(56) References Cited

PUBLICATIONS

Wang et al., Dietary supplementation with blueberries, spinach, or spirulina reduces ischemic brain damage, Experimental Neurology, 2005, 193, 75-84.

Bunea et al, Total and individual carotenoids and phenolic acids content in fresh, refrigerated and processed spinach (*Spinacia oleracea* L.), Food Chemistry 2008, 108, 649-656.

Park et al., Antidiabetic Activity of Fruits and Vegetables Commonly Consumed in Korea: Inhibitory Potential against α-Glucosidase and Insulin-like Action in vitro, Food Sci. Biotechnol. 2012, 21(4): 1187-1193.

Seidlova-Wuttke et al., Plant derived alternatives for hormone replacement therapy (HRT), Horm Mol Biol Clin Invest, 2013, 16(1): 35-45.

Lakshminarayana et al., Determination of Major Carotenoids in a Few Indian Leafy Vegetables by High-Performance Liquid Chromatography, Journal of Agricultural and Food Chemistry, 2005, 53, 2838-2842.

Maeda et al., Effects of DNA polymerase inhibitory and antitumor activities of lipase-hydrolyzed glycolipid fractions from spinach, Journal of Nutritional Biochemistry, 2005, 16, 121-128.

Negishi et al., Antigenotoxic activity of natural chlorophylls, Mutation Research, 1997, 376, 97-100.

Lomnitski et al., Composition, Efficacy, and Safety of Spinach Extracts, Nutrition and Cancer published online, Nov. 18, 2009.

Franke et al., Vitamin C and flavonoid levels of fruits and vegetables consumed in Hawaii, Journal of Food Composition and Analysis 17, 2004, 17, 1-35.

Edenharder et al., Isolation and Characterization of Structurally Novel Antimutagenic Flavonoids from Spinach (*Spinacia oleracea*), J. Agric. Food Chem. 2001, 49, 2767-2773.

Kuriyama et al., Inhibitory effects of glycolipids fraction from spinach on mammalian DNA polymerase activity and human cancer cell proliferation, Journal of Nutritional Biochemistry, 2005, 16, 594-601.

Joseph et al., Reversals of Age-Related Declines in Neuronal Signal Transduction, Cognitive, and Motor Behavioral Deficits with Blueberry, Spinach, or Strawberry Dietary Supplementation, The Journal of Neuroscience, Sep. 15, 1999, 19(18), 8114-8121.

Gupta et al. Amelioration of $CCl_4$ induced hepatosuppression by Spinacia oleracea L. leaves in wistar albino rats, Pharmacologyonline, 2006, 3: 267-278.

Beresford et al, Risk of endometrial cancer in relation to use of oestrogen combined with cylic progestagen therapy in postmenopausal women, The Lancet, Feb. 15, 1997, vol. 349, p. 458.

Riggs et al., Selective Estrogen-Receptor Modulators—Mechanisms of Action and Application to Clinical Practice, N. Engl. J. Med,Feb. 13, 2003, 348(12): 1192, pp. 618-629.

Grady et al., Hormone Replacement Therapy and Endometrial Cancer Risk: A Meta-Analysis, Obstetrics & Gynecology, 1995, 85, 302-313.

Delmas, Treatment of postmenopausal osteoporosis, The Lancet, 2002, vol. 359, 2018-2026.

Taylor et al., Alkaloids From Courbonia Glauca Rhizome, Phytochemistry, 1973, vol. 12, 1178-1180.

Nyska et al., Slowing Tumorigenic Progression in TRAMP Mice and Prostatic Carcinoma Cell Lines Using Natural Anti-Oxidant from Spinach, NAO—A Comparative Study of Three Anti-Oxidants, Toxicologic Pathology, 2003, vol. 31, pp. 39-51.

Bhatia et al., Spinacia oleracea L. protects against gamma radiations: a study on glutathione and lipid peroxidation in mouse liver, Phytomedicine, 2004, 11, 607-615.

Nyska et al., Topical and oral administration of the natural water-soluble antioxidant from spinach reduces the multiplicity of papillomas in the Tg.AC mouse model, Toxicology Letters, 2001, 122, 33-44.

\* cited by examiner

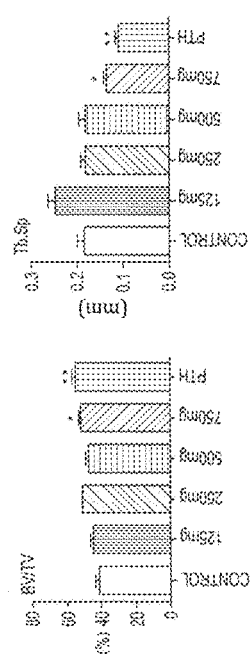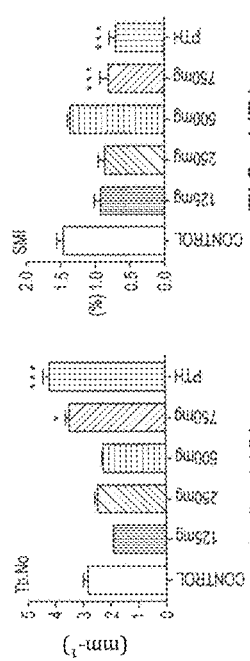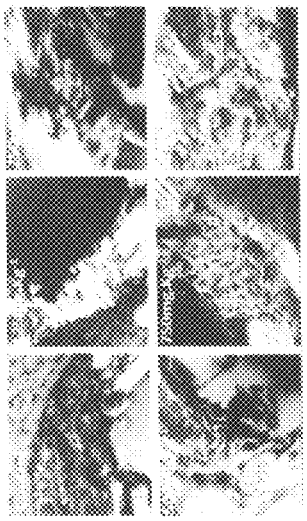

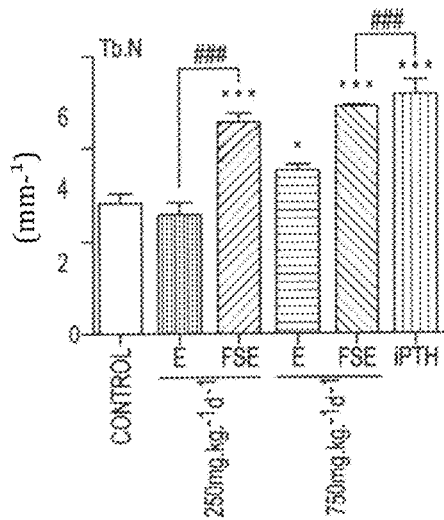 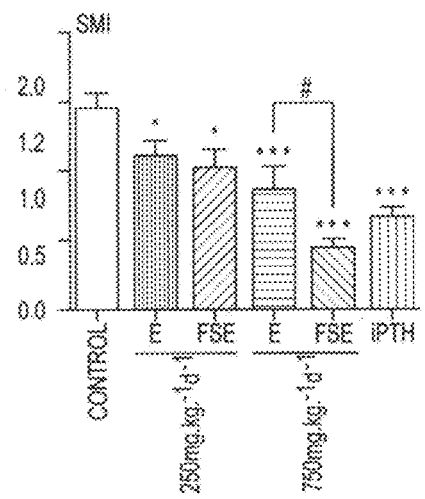
FIG. 2(C)　　　　　FIG. 2(D)
FIG. 2(E)
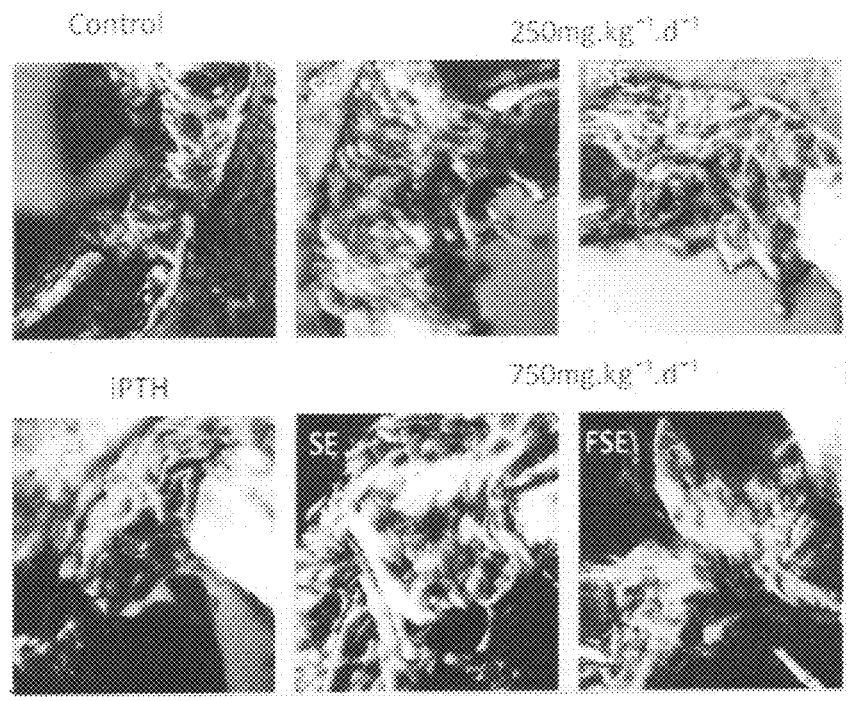

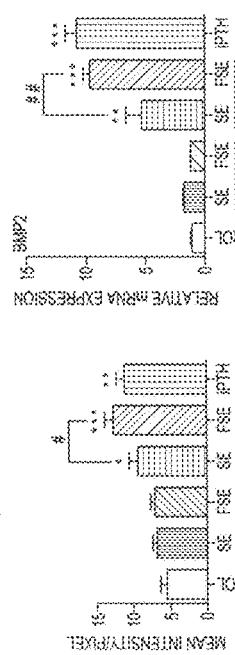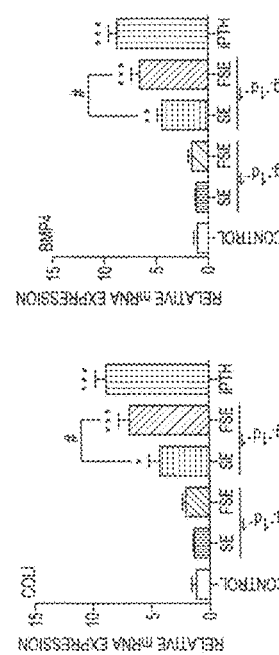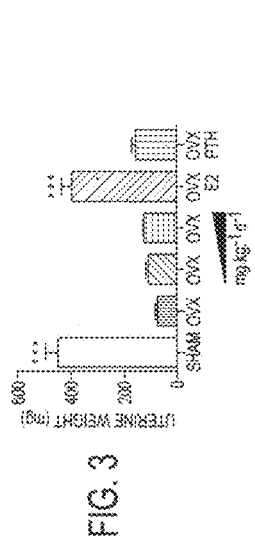

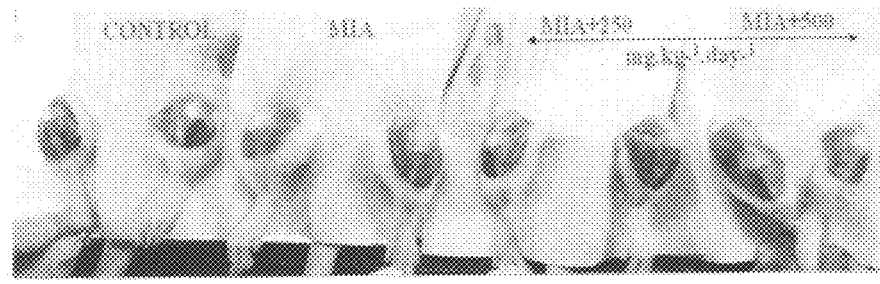
FIG. 6(A)
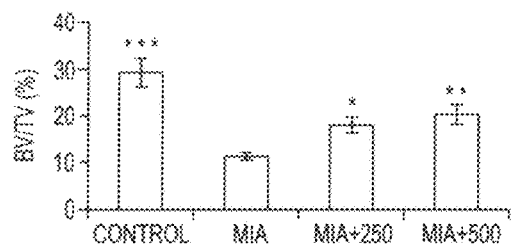
FIG. 6(B)
FIG. 6(C)
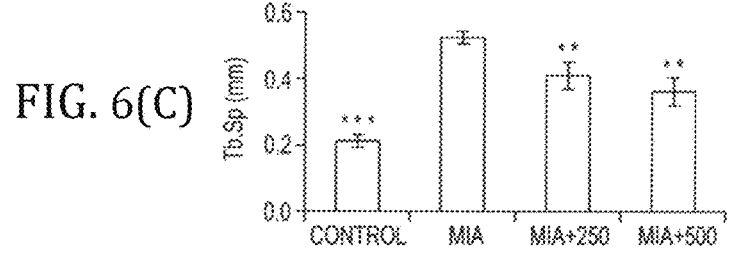
FIG. 6(D)
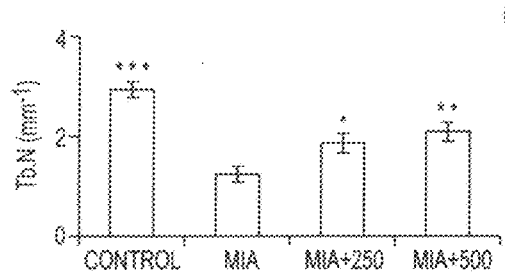
FIG. 6(E)
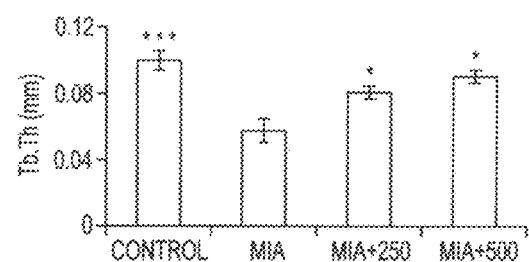

FORMULATION FOR THE PREVENTION AND TREATMENT OF BONE RELATED DISORDERS

FIELD OF THE INVENTION

The present invention relates to a formulation of *Spinacea oleracea* useful for the prevention or treatment of osteo-health related disorders. The present invention relates in the field of pharmaceutical formulation that provides extract, fractions, pure compound isolated from natural sources and formulation thereof useful for the prevention and treatment of various medical indications. Further, this invention relates to conditions associated with estrogen dependent or independent diseases (primary/secondary osteoporosis) or syndromes or disorders preferably relating to cartilage such as osteoarthritis caused in humans and animals. Furthermore, this invention relates to achievement of peak bone mass during skeletal growth and health in humans and animals. Particularly, the present invention relates to the processes for the preparation of biologically active extracts, from *Spinacea oleracea* from the family Amaranthaceae their pharmaceutically acceptable excepients and compositions of the principal aspect of the present invention.

BACKGROUND OF THE INVENTION

The post-menopausal period in women's life is challenging for their health and is associated with increased risk of musculoskeletal impairments. Women undergoing the menopausal transition experience both, age as well as gonadal hormone related changes in physiological functions. As a result, accelerated loss in bone mass density (BMD), muscle mass and muscle strength occur in women undergoing menopause, unlike men of the same age. The common musculoskeletal disorders among postmenopausal women (PMW) are osteoporosis, osteoarthritis (OA). Postmenopausal women with osteoarthritis have a 20% increased risk of fracture and experience 25% more falls than those without osteoarthritis (Prieto-Alhambra et al. 2013).

The risk is high in women as compared to men and increases sharply after 50 years of age. The quality of life is greatly impaired in persons with sever osteoporosis. It is known to affect >50% of women and 30% men over the age of 50 years. The reduction in bone strength associated with this disease markedly increases the risk of fractures, and the consequent pain and loss of function have adverse effect on the quality of life. For fractures and osteoarthritis there are no drugs in the market.

Most of the pharmacological agents available for clinical use for osteoporosis are calcium, vitamin D and its analogue, calcitonin, bisphosphonates, raloxifene, hormone replacement therapy (HRT) etc. act by decreasing the rate of bone resorption, thereby slowing the rate of bone loss. Timely administration of such antiresorptive agents prevents bone loss. Hormone replacement therapy, though effective in preventing bone loss following ovariectomy or menopause in women, is associated with increased risk of endometrial hyperplasia and carcinoma [Grady, D. Grebretsadik, T. Ernestwr, V. Petitti, D. *Gynecol.* 85, 304-313 (1995), Beresford S. A. Weiss, N. S. Voigt, L. F. McKnight, B. *Lancet* 349, 458-461 (1997)], breast cancer [Riggs, L. Hartmann, L. C. *J. Med.* 348, 618-629, (2003)], and thromboembolic diseases [Delmas, P. D. *Lancet* 359, 2018-2026 (2002)]. Bisphosphonates are poorly absorbed and may cause gastrointestinal irritation, diarrhoea and constipation. Raloxifene has been reported to increase incidence of hot flashes, deep vein thrombosis, pulmonary embolism and leg cramps [Clemett, D., Spencer, C. M. *Drugs* 60, 380-409 (2000)]. Though anti-resorptive therapies are available and are in use, anabolic/osteogenic therapies are limited to PTH, NaF and strontium which are also accompanied by undesirable side effects (Rosen and Bilezikian 2001, Lane and Kelman 2003). Thus there is a need for the development of agents that could increase bone mass and strength, thereby reducing the risk of osteoporotic fracture more than the currently available anti-resorptive agents.

The importance of traditional medicine as a source of primary health care was first officially recognized by the World Health Organization (WHO) in 1976 by globally addressing its Traditional Medicine Programme. In traditional medicine, there are many natural crude drugs that have the potential to treat bone diseases. However, not much laboratory work has been reported evaluating their possible development and use, except ipriflavone, a natural product derivative, which has been used clinically for such indications [Fujita, T., Yoshikawa, S., Ono, K., Inoue, T., Orimo, H. *J. Clin. Exp. Med.* 138, 113-141 (1986), Passeri, M., Biondi, M., Costi, D., Bufalino, L., Castiglione, g. N., DiPeppe, C., Abate, G. *Bone Miner.* 19 (Suppl. 1), S57-62 (1992)]. It is believed that herbal medicines are easily available, less expensive, and safer than chemically synthesized drugs. In India Ayurvedic medicine emerged during the rise of the philosophies of the Upanishads, Buddhism, and other schools of thought in India. Herbs played an important role in Ayurvedic medicine. In our program search for natural osteogenic plant, n-butanol soluble fraction of ethanol extract of *Dalbergia sissoo* aerial part which is renewable source exhibited osteogenic activity in our test model. Thus, the plant extract might possess bioactive ingredients that could promote bone formation. The effects on osteoporosis and total osteo-health and related disorders and has not been explored.

There is, thus, an urgent need to discover and develop a promising herbal product exhibiting promising bone anabolic or for bone forming activity in experimental animals and human beings for osteoporosis and osteoarthritis. The *Spinacia oleracea* is a fit case to study and explore its true potential with respect to its bone forming response of its extract, fraction and pure biologically active marker components. The experiments have shown that its extract exhibit promising bone forming activity.

*S. oleracea* L. commonly known as *Spinacea*, is an edible flowering plant in the family of Amaranthaceae. It is an erect herb about 30-60 cm height, native to South-West Asia and cultivated throughout world as vegetables. Fresh plants are boiled and eaten to increase appetite and as vitamin supplement. Although less in calorific value, *spinacea* is recommended as the best source of iron, vitamins, minerals and mineral salts, 100 g of *spinacea* provide more than 20% of the daily Value of vitamin A, C and vitamin K, magnesium, manganese, folate and iron and 10-19% of the daily Value of B vitamins, riboflavin and vitamin B6, vitamin E, calcium, potassium especially when fresh or quickly boiled. [The wealth of India. Vol 5. New Delhi: National Institute of Science, Communication & Information Resources (CSIR), 2004: pp 146-7].

Ayurveda and Unani system of medicine describe the plant as carminative, laxative, alexipharmic, leaves are emollient, antipyretic, diuretic, maturant, laxative, digestible, anthelmentic useful in diseases of blood and brain, asthma, leprosy, biliousness, urinary concretion, leucorrhoea, inflammation of the lungs and the bowels, sore throat, pain in joints, thirst, lumbago, cold and sneezing, sore eye, ring worm scabies, leucoderma, soalding urine, arrest vomiting, biliousness, flatulence and in the treatment of febrile conditions. Seeds are also used in the treatment of difficulty in breathing, inflammation of the liver and jaundice urinary calculi.

Different parts of *spinacea* and extracts have been demonstrated to exert numerous beneficial effects such as antioxidative, hepato-protective, anti-inflammatory, anticancer, chemo-protective, central nervous system protection and anti-aging functions. Consumption of polyphenols rich fresh vegetables has been associated with a reduced risk of oxidative stress-induced disease. Water extracts of *spinacea* leaves demonstrated their biological activity in both in vitro and in vivo systems [Lomnitski, L., Bergman, M., Nyska, A., Ben-Shaul, V., Grossman, S. *Nutr Cancer* 2003, 46, 222-231]. Maximum antioxidant effect was exhibited in the ethanol fraction (11.55%) followed by ethyl acetate fraction (10.51%) n-hexane fraction (4.12%) antioxidant activity in dose-dependent way in DPPH radical scavenging assey [Arfan, M., Gul, S., Usman, R., Khan, A., Rauf, A., Muhammad, N., Shah, S. U. A., Khan, A., Ali, M. *Academic J of Plant Sci.* 2013, 6, 3]. Recovered antioxidant flavonoids, in particular spinacetin and petuletin, content from a crude *spinacea* extract by the elimination of a major part of non-phenolic components by adsorption procedure exhibited significantly increased antioxidant efficiency in nitro blue tetrazolium (NBT) assay and the diphenyl-2-picrylhydrazyl (DPPH) radical scavenging assey [Aehle, E., Raynaud-Le Grandic, S., Ralainirina, R., Baltora-Rosset, S., Mesnard, F., Prouillet, C., Mazière, J. C., Fliniaux, M. A., *Food Chem.* 2004, 86, 579-585].

A water-soluble natural antioxidant mixture (NAO) isolated from *spinacea* leaves specifically inhibits the lipoxygenase enzyme [Lomnitski, L., Bergman, M., Nyska, A., Ben-Shaul, V., Grossman, S., *Nutr Cancer* 2003, 46, 222-231]. *Spinacea* extracts has beneficial effects on body weight and serum lipids in obese postmenopausal and premenopausal women and in men. Ecdysone is produced by *spinacea* and *spinacea* extracts containing ecdysone decreased body fat load, thereby reducing secretion of proinflammatory cytokines by visceral adipocytes and oxidative stress [Seidlova-Wuttke, D., Jarry, H., Wuttke, W., *Horm. Mol. Biol. Clin. Invest.* 2013, 16, 35-45].

Supplementation of plant extract, extracted with 50% methanol to mice for 15 days showed radioprotective effect against gamma radiation-induced oxidative stress the check of radiation-induced damage in mice liver at the optimum dose of 1100 mg/kg body wt./day [Bhatia, A. L., Jain, M., *Phytomedicine* 2004, 11, 607-615]. Pretreatment with alcoholic extract prior to the administration of $CCl_4$, at the doses of 100 and 200 mg/kg/day, for 7 days, significantly restored to all the serum and liver parameters, serum-marker enzymes like GGT, AST, ALT, LDH, SDH, GDH, ALP, near to the normal levels [Gupta, R., Singh, D. *Pharmacologyonline* 2006, 3, 267-278; Al-Dosari, M. S. Clinical and Experimental Medical Journal 2010, 4, 129-140]. Additionally, n-butanol fraction of *Spinacia oleracea* showed significant protection against CCl4-induced hepatotoxicity. The presence of 20-hydroxyecdysone (20-HE) in the n-butanol fraction of *Spinacia oleracea* further confirmed by HPTLC analysis may be responsible the effects [Jain, N. K., Singhai, A. K., *Asian Pac. J. Trop. Biomed.*, 2012, 2, S232.].

*Spinacea* extract and natural antioxidant mixture (NAO) isolated from *spinacea* have shown anticancer effect on various types of cancer such as ovarian, lung, prostatic, breast and colon. *Spinacea* showed antiproliferative activities in-vitro using HepG(2) human liver cancer cells [Chu, Y.-F., Sun, J., Wu, X., Liu, R. H., *J Agric. Food Chem.*, 2002, 50, 6910-6916].

*Spinacea* extract NAO was tested both in-vivo and in-vitro in cell lines DU145 and PC3 derived from human prostate and in the TRAMP (Transgenic Adenocarcinoma Mouse Prostate) model for prostatic cancer chemoprevention. NAO exerted an antiproliferative effect on DU145 and PC3 cells. Inhibition of cellular proliferation occurred in a dose-dependent manner ($IC_{50}$ in the range of 2-4 mM), increasing numbers of G1 cells and reducing hydrogen peroxide and peroxide levels. [Nyska, A., Suttie, A., Bakshi, S., Lomnitski, L., Grossman, S., Bergman, M., Ben-Shaul, V., Crocket, P., Haseman, J. K., Moser, G. *Toxicol Pathol* 2003, 31, 39-51] *Spinacea* is a rich source of chlorophyll and Chlorophyllin, a water-soluble form of chlorophyll, is interesting for its antimutagenic and anticarcinogenic properties [Negishi, T., Rai, H., Hayatsu, H. *Mutat Res* 1997, 376, 97-100]. Topical (2 mg) and oral (100 mg/kg) NAO-treatment to hemizygous Tg.AC mice for 5 days/week for 5 week revealed a significant decrease in multiplicity in mouse skin papilloma in the NAO topically treated group. The effect of NAO in the Tg.AC model may be related to its ability to detoxify peroxides and free radicals [Nyska, A., Lomnitski, L., Spalding, J., Dunson, D. B., Goldsworthy, T. L., Grossman, S., Bergman, M., Boorman, G. *Toxicol. Let.,* 2001, 122, 33-44].

DNA polymerase inhibitors could be employed as anticancer chemotherapy agents because they inhibit cell proliferation. *Spinacea* contained the large amount of sulfoquinovosyl diacylglycerol (SQDG). Fraction containing the major glycolipids in monogalactosyl diacylglycerol, digalactosyl diacylglycerol and sulfoquinovosyl diacylglycerol (SQDG) from dried vegetables inhibited of DNA polymerase α (pol α) in-vitro and also the proliferation of human cancer cells (inhibition of pol α activity may lead to cell growth suppression,). human stomach cancer cells (NUGC-3) and promyelocytic leukemia (HL-60). The inhibitory effect glycolipids fractions of NUGC-3 was almost equal as that of HL-60. The inhibition by the *spinacea* glycolipids fraction was dependent on dose, and the $LD_{50}$ value was 66.8-70.1 µg/ml. both for NUGC-3 and HL-60 cell line [Kuriyama, I., Musumi, K., Yonezawa, Y., Takemura, M., Maeda, N., Iijima, H., Hada, T., Yoshida, H., Mizushina, Y., *J Nutr Biochem* 2005, 16, 594-601; Maeda, N., Hada, T., Murakami-Nakai, C., Kuriyama, I., Ichikawa, H., Fukumori, Y., Hiratsuka, J., Yoshida, H., Sakaguchi, K., Mizushina, Y. *J Nutr Biochem* 2005, 16, 121-128].

Antioxidant effects associated with *spinacea* have a protective effects on neurodegenerative disorders such as ischemia and aging by scavenging reactive oxygen species, generated during cerebral ischemia and reperfusion. Adult male Sprague-Dawley rats were fed with *spinacea* extract with control diet for 4 weeks had reduced cerebral infarction after ischemia and reperfusion. [Wang, Y., Chang, C.-F., Chou, J., Chen, H.-L., Deng, X., Harvey, B. K., Cadet, J. L., Bickford, P. C. *Exp. Neurol.* 2005, 193, 75.]. Moreover, supplementation of diet with *spinacea* improve learning and memory in aged animals and possibly in humans and reverse age-induced dwindle in beta-adrenergic receptor function in cerebellar Purkinje neurons [Bickford, P. C., Gould, T., Briederick, L., Chadman, K., Pollock, A., Young, D., Shukitt-Hale, B., Joseph, J. *Brain Res* 2000, 866, 211-217; Joseph, J. A., Shukitt-Hale, B., Denisova, N. A., Bielinski, D., Martin, A., McEwen, J. J., Bickford, P. C. *J Neurosci* 1999, 19, 8114-8121].

Spinacea extract a dose of 400 mg/kg body weight decreased significantly the blood glucose and increased significantly insulin concentrations comparable to standard drug, chlorpropamide [Karami Bonari, A. R. *Clinical Biochemistry* 2011, 44, S331]. Moreover, α-glucosidase inhibitory activity, insulin like action, insulin sensitizing activity exhibited by whole juice and ethanolic extract. Whole juice samples of *spinacea* showed 5.2% α-glucosidase inhibition at 50 of the juice solution [Park, J.-H., Kim, R.-Y., Park, E. *Food Sci. Biotechnol.* 2012, 21, 1187-1193.] Ethanolic extract of *Spinacia oleracia* leaves in alloxan induced diabetic rat showed 54% decrease in serum glucose level compared to control at 100 mg/kg [Kumar, N. J., Loganathan, Glob. J. Biotech.Biochem. 2010, 5, 87-91], additionally hypoglycaemic activity evaluation of ethanolic and aqueous extract of (200 & 400 mg\kg). by Gomathi et al. resulted in a significant decrease in the elevated blood glucose levels as compared to the control. Studies showed regeneration of β-cells of pancreas improvement in body weight and serum lipid profile [V. Gomathi, B. Jayakar, R. Kothai, G. Ramakrishnan, Antidiabetic activity of leaves of *Spinacia oleracea* Linn. in Alloxan-induced diabetic rats. J. Chem. Pharm. Res., 2010, 2, 266-274].

Pure Cell Complex (PCT-233), corresponds to the isolation and stabilization of the photosynthetic machinery of the thylakoid membrane from mesophyll tissue of *spinacea* leaves, was extracted from *spinacea* leaves [Purcell M. Procedure for preparing active plant extracts used to trap free radicals, the extracts and compounds and devices containing them. Canadian patent: CA 2293852, 1999) PCT], is able to protect IMR-32 cells (human neuroblastoma) from apoptosis caused by the generation of reactive oxygen species (ROS) and singlet oxygen.

Aqueous extract of leaves is effective in almost all the symptoms of inflammatory bowel disease (chronic idiopathic inflammatory intestinal condition characterized by intestinal inflammation and mucosal damage). Treatment with aqueous extract of leaves (500 and 1,000 mg/kg/day) to acetic acid and ethanol induced colitis in mice showed significant increase in body weight, decrease in diarrhea with bloody stool, and increase in hemoglobin in inflammatory bowel disease [Otari, K. V., Gaikwad, P. S., Shete, R. V., Upasani, C. D. *Inflammopharmacology* 2012, 20, 277-287].

Natural antioxidant mixture (NAO) isolated from *spinacea* exhibited cardio-protection against Doxorubicin (DOX) induced cardiotoxicity. BALB/C mice were treated with NAO (10 mg/kg, ip) for seven consecutive days before and/or 6 days after DOX administration. NAO at the dose of 130 mg/kg conferred significant cardiac protection [Breitbart, E., Lomnitski, L., Nyska, A., Malik, Z., Bergman, M., Sofer, Y., Haseman, J. K., Grossman, S. *Hum Exp Toxicol* 2001, 20, 337-345] The methanolic extract fresh plant leaves of *Spinacia oleracea* was found to be highly active against UTI causing bacteria such as *Escherichia coli, Enterococcus faecalis, Klebsiella pneumonia* to cure urinary tract infection [Das, M. P., Chatterjee, S. Int. J. Pharm. Sci. Rev. Res., 23, 2013, 23, 211-215].

Previous Phytochemical Investigations

Phytochemical screening of the extract of *Spinacia oleracea* revealed the presence of alkaloids, glycosides, proteins and amino acids, sterols, carbohydrates, phenolic compounds, flavonoids, saponins, and tannins [Das, M. P., Chatterjee, S. *Int. J. Pharm. Sci. Rev. Res.* 2013, 23, 211-215]. Several types of compounds have been isolated from different parts of *Spinacia oleracea*. The dry *spinacea* powder extracted with mixture of methanol/water (70:30) (v/v) afforded flavonoid class of compounds. All compounds characterized as 5,3'-dihydroxy-4'-methoxy-6,7-methylene dioxyflavonol 3-O-β-glucuronide, 5,2',3'-trihydroxy-4'-methoxy-6,7-methylenedioxyflavonol 3-O-β-glucuronide, 5-hydroxy-3',4'-dimethoxy-6,7-methylenedioxyflavonol 3-O-β-glucuronide, 5,6,3'-trihydroxy-7,4'-dimethoxyflavonol 3-O-β-glucuronide, 5,6-dihydroxy-7,3',4'-trimethoxyflavonol 3-O-β-glucuronide, 5,6,4'-trihydroxy-7,3'-dimethoxyflavonol 3-O-disaccharide, 5,6,3',4'-tetrahydroxy-7-methoxyflavonol 3-O-disaccharide, 5,8,4'-trihydroxy flavanone, 7,8,4'-trihydroxyflavanone have shown antimutagenic activity [Edenharder, R., Keller, G., Platt, K. L., Unger, K. K., *J. Agric. Food Chem.* 2001, 49, 2767-2773]. *S. oleracea* is rich in unique flavonoid compounds patuletin and its derivatives, instead of flavonoids widespread in plants such as kaempferol, quercetin, myricetin, apigenin and luteolin. Patuletin (quercetagetin 6-methyl ether), spinacetin (quercetagetin 6,3'-dimethyl ether) and 6-methoxykaempferol have been isolated from *spinacea* leaves [Zane, E., Wender, S. H., *J. Org. Chem.* 1961, 26, 4718-4719; Bescia, M., Leonte, A., Oancea, I. *Bul Univ Galati Fasc* 1982, 63, 79-83, Chemistry Abstract, 96, 84312, Wiermann, R., Wollenweber, E., Rehse, C. *Journal of Biosciences*, 1981, 36, 204-206]. Spinatoside (3,6-dimethoxy-5,7,3',4'-tetrahydroxyflavone 4'-O-β-D-glucopyranuronide) [Wagner, H., Maurer, J., Farkas, L., & Strelisky, J. *Tetrahedron*, 1977, 33, 1405-1409] and three new flavonol glycosides, namely patuletin 3-O-β-D-glucopyranosyl-(1→6)-[β-D-apiofuranosyl-(1→2)]-β-D-glucopyranoside, patuletin 3-O-β-D-glucopyranosyl, patuletin 3-O-β-gentiobioside and spinacetin 3-O-β-gentiobioside have been isolated from polar fraction of methanolic extract of *spinacea* leaves. [Aritomi, M., Komori, T., Kawasaki, T. *Phytochemistry* 1986, 25, 231-234; Ferreres, F Castaner, M., & Tomas-Barberan, F. A. *Phytochemistry* 1997, 45, 1701-1705].

In a HPLC analysis of extract of *S. oleracea* showed that the presence of patuletin-3-glucosyl-(1→6)[apiosyl(1→2)]-glucoside, spinacetin-3-glucosyl-(1→6)[apiosyl(1→2)]-glucoside, patuletin-3-(2"-feruloylglucosyl)(1→6)-[apiosyl-(1→2)]-glucoside, spinacetin-3-(2"-feruloyl glucosyl)(1→6)[apiosyl(1-2)]-glucoside, patuletin-3-gentiobioside substituted with feruloyl, probably a compound of patuletin with gentiobioside and rhamnoside, spinatoside-4'-glucuronide, 5,3',4'-trihydroxy-3-methoxy-6,7-methylenedioxyflavone-4'-glucuronide, 5,4'-dihydroxy-3,3'-dimethoxy-6,7-methylenedioxyflavone-4'-glucuronide [Ferreres, F., Castaner, M., & Tomas-Barberan, F. A. *Phytochemistry* 1997, 45, 1701-1705; Bergquist, S. A. M., Gertsson, U. E., Knuthsen, P., Olsson, M. E., *J. Agric. Food Chem.* 2005, 53, 9459-9464] and spinacetin-3-O-β-D-(2"-feruloylglucopyranosyl) (1→6)-β-D-glucopyranoside [Gil, M., Ferreres, F., Francisco A. T. B. *J. Agric. Food Chem.* 1999, 47, 2213-2217]. Three highly oxygenated flavonoids glucuronides 5,3',4'-Trihydroxy-3-methoxy-6,7-methylenedioxyflavone 4'-β-D-glucuronide, 5,4'-dihydroxy-3,3'-dimethoxy-6,7-methylenedioxyflavone 4'-β-D-glucuronide and 5,7,4'-trihydroxy-3,6,3'-trimethoxyflavone 4'-β-D-glucuronide (jaceidin) have been isolated from methanolic extract of fresh leaves of *S. oleracea* via Droplet counter-current chromatographic method [Aritomi, M., Kawasak, T., *Phytochemistry* 1984, 23, 2043-2047]. Three phenolic acids ortho-coumaric acid, ferulic acid and para-coumaric acid along with some carotenoids lutein, β-carotene, violaxanthin and neoxanthin were depicted in LC-MS analysis of *spinacea* extract [Bunea, A., Andjelkovic, M., Socaciu, C., Bobis, O., Neacsu, M., Verhe, R., Camp, J. V. *Food Chemistry* 2008, 108, 649-656; Lakshminarayana, R., Raju, M., Krishnakantha, T. P., Baskaran, V., *J. Agric. Food Chem.* 2005, 53, 2838-2842]. Reports shown that the presence of kaempferol, myricetin, quercetin [Franke, A. A., Custer, L. J Arakaki, C., Murphy, S. P. *Journal of Food Formulation and Analysis* 2004, 17, 1-35; Sultana, B., Anwar, F. *Food Chemistry* 2008, 108, 879-884; Dehkharghanian, M., Adenier, H., Vijayalakshmi, M. A. *Food Chemistry* 2010, 121, 863-870] along with two flavones apigenin and luteolin in *spinacea* leaves extract [Dehkharghanian, M., Adenier, H., Vijayalakshmi, M. A. *Food Chemistry* 2010, 121, 863-870]. The phytochemical investigation of seeds of *Spinacia oleracea* showed the presence of 20-hydroxyecdysone and polypodine B. It also contain a compound with properties similar to those of 24(28)-dehydromakisterone A and a small amount of ecdysone [Bathoky, M., Toth, I., Szendrei, K., Reisch, J. *Phytochemistry,* 1982, 21, 236-238]. A sterol was isolated from *spinacea* and subsequently characterized as α-spinasterol [Heyl, F. W., Wlese, E. C., Speer, J. H. *J. Biol. Chem.* 1929, 82, 111; Hart, M. C., Heyl, F. H., *J. Biol. Chem.* 1932, 95, 311,] and further phytochemical investigations showed the presence of other sterols name as stigmastenol and stigmastanol [Dawidar, A. M., Amer, M. A., *Phytochemistry* 1973, 12, 1180-1181; Khauna, I., Seshadn, R., Seshadn, T. R. *Phytochemistry* 1974, 13, 199]. The presence of $\Delta^5$-sterol stigmasterol in *S. oleracea* seed oil has been observed in small quantity and the occurrence of β-sitosterol in minute proportions was presumed [Itoh, T., Tamura, T., Matsumuto, T. *Lipids* 1974, 9, 173,]. *Spinacia oleracea* contains high concentration of vitamin A, E, C, and K and also folic acid, oxalic acid [Guha, D., Das, S., Indian *J. Exp. Biol.* 2008, 46, 185-190]. Along with these chemicals various minerals present in the *spinacea*. These are magnesium, manganese, calcium, phosphorus, iron [Guha, D., Das, S., *Indian J. Exp. Biol.* 46, 185-190, 2008], zink, copper and potash [The wealth of India. Vol 5. New Delhi: National Institute of Science, Communication & Information Resources (CSIR), 2004: pp 146-7]. The present invention focuses on preparation of standardized extract of *Spinacea oleracea* that significantly improves estrogen dependent or independent diseases or syndromes or disorders caused in humans and animals, and further achievement of peak bone mass during skeletal growth and health including osteoarthritis through oral route of administration from abundantly available renewable source.

Objects of the Invention

The main object of the present invention is to provide a formulation comprising;
a. an extract and/or a fraction comprising compounds 5,3',4'-trihydroxy-3-methoxy-6,7-methylenedioxy-flavone in the range of 0.01 to 0.07% and 5,7,3',4'-tetrahydroxy-3,6-dimethoxy-flavone in the range of 0.004-0.05%;
b. pharmaceutically acceptable carriers and additives;
c. surfactant; and
d. co-surfactant,
wherein extract and/or fraction is obtained from Spinach and the formulation is used in prevention and/or treatment of bone related disorders.

Yet another object of the present invention is to provide the n-ethanol soluble fraction derived from *Spinacea oleracea* in pharmaceutically acceptable form in order to enhance its application potential for the management or prevention or treatment or cure of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals.

Still another object of the present invention is to provide the n-ethanol soluble fraction derived from *Spinacea oleracea* having bone anabolic (i.e. new bone formation) effect rather than anti-resorptive (stopping further bone loss) effect.

Yet another object of the present invention is to provide, a formulation devoid of uterine estrogenicity.

One more objective of the invention is to provide compounds which are non toxic to the cells.

Yet another object of the invention is to provide a pharmaceutically acceptable formulation of *Spinacia oleracea*.

Yet another object of the invention is to provide a pharmaceutically acceptable formulation of *Spinacia oleracea*.

Yet another object of the present invention is to provide a formulation comprising *Spinacia oleracea* extract which may be administered orally.

SUMMARY OF THE INVENTION

Accordingly the present invention provides a formulation comprising;
a. an extract and/or a fraction comprising compounds 5,3',4'-trihydroxy-3-methoxy-6,7-methylenedioxy-flavone in the range of 0.01 to 0.07% and 5,7,3',4'-tetrahydroxy-3,6-dimethoxy-flavone in the range of 0.004-0.05%;
b. pharmaceutically acceptable carriers and additives;
c. surfactant; and
d. co-surfactant,
wherein extract and/or fraction is obtained from Spinach and the formulation is used in prevention and/or treatment of bone related disorders.

Further the formulation is useful for the prevention or treatment of estrogen dependent or independent diseases or syndromes or disorders caused in humans and animals, and achievement of peak bone mass during skeletal growth and health in humans and animals.

In an embodiment of the present invention it provides a formulation wherein the spinach is *Spinacea oleracea*.

In an embodiment of the present invention it provides a formulation wherein the fraction and/or extract comprises, solvents selected from the group consisting of ethanol, butanol, ethyl acetate, hexane, carbon dioxide or mixture thereof.

In an embodiment of the present invention it provides a formulation wherein the formulation is a nanoemulsion preconcentrate (SMEDDS).

In an embodiment of the present invention it provides a formulation wherein the pharmaceutically acceptable carrier is selected from the group comprising of oleic acid, castor oil, polyoxyethylene sorbitan monopalmitate (such as referred to by the trademark TWEEN®40), polyoxyethylene sorbitan monostearate (such as referred to by trademark TWEEN® 60), polyoxyethylene sorbitan monooleate (such as referred to by the trademark TWEEN® 80), sorbitan monopalmitate (such as referred to by the trademark SPAN® 40), sorbitan monostearate (such as referred to by the trademark SPAN® 60), polyethylene glycol 400 (PEG 400), polyethylene glycol 600 (PEG 600), Propylene Glycol, Ethanol etc.

In an embodiment of the present invention it provides a formulation wherein pharmaceutically acceptable additives is selected from the group comprising of microcrystalline cellulose, crospovidone, cross-linked povidone and commercially available polyvinylpyrrolidone (PVP, Povidone), low-substituted hydroxypropylcellulose, alginic acid, carboxymethylcellulose, calcium salts and sodium salts, fumed silica (colloidal silica), guar gum, magnesium aluminum silicate, methylcellulose, powdery cellulose, starch and sodium alginate etc.

In an embodiment of the present invention it provides a formulation wherein the surfactant/co-surfactant is selected from the group comprising of Sorbitan esters, polysorbates, polyether compounds etc.

In an embodiment of the present invention it provides a formulation wherein the extract is given at a dose in the range of 250 to 750 mg·kg$^{-1}$·day$^{-1}$ to treat or prevent bone disorder.

In an embodiment of the present invention it provides a formulation wherein the fraction is given at a dose in the range of 25 to 200 mg·kg$^{-1}$·day$^{-1}$ to treat or prevent bone disorder.

In an embodiment of the present invention it provides a formulation wherein the formulation is used for prevention and/or treatment of bone related disorders or osteo-health related disorders including fractures, postmenopausal osteoporosis, mitigation of swelling, inflammation, pain and further in regeneration of cartilage useful in the prevention and/or treatment of osteoarthritis.

In an embodiment of the present invention it provides a formulation wherein the formulation is used as a chondroprotective agent.

In an embodiment of the present invention it provides a formulation wherein the formulation has bioavailability, is enhanced by, more than 10 fold as compared to the extract and fraction.

In an embodiment of the present invention it provides a formulation wherein the formulation of extract enhances bone volume/tissue volume by around 24%.

In an embodiment of the present invention it provides a formulation wherein the formulation of fraction enhances bone volume/tissue volume by around 68%.

In yet another embodiment of the present invention it provides a process for preparation of the formulation, comprising the steps of:
 a) powdering the leaves of the plant *Spinacea oleracea*;
 b) percolating the powder obtained in step (a) with solvent for a period of up to 24 hrs followed by collecting the percolate;
 c) repeating the step (b) for 4 to 8 times at a temperature in the range of 18-25° C. to obtain the alcoholic extract A001;
 d) fractioning the extract obtained in step (c) with n-hexane to obtain hexane soluble fraction and hexane insoluble residue;
 e) triturating the hexane insoluble residue as obtained in step (d) with chloroform to obtain chloroform soluble fraction and chloroform insoluble residue;
 f) suspending the chloroform insoluble residue as obtained in step (e) with water followed by extracting with n-butanol to obtain n-butanol soluble fraction F004;
 g) dissolving the spinach extract (40 to 50% w/w) obtained in step (c) in 50 to 150 mL of surfactant mix;
 h) optionally dissolving the fraction (40 to 50% w/w) obtained in step (f) in 50 to 150 mL of surfactant mix to obtain the formulation.

In an embodiment of the present invention it provides a formulation wherein the surfactant/co-surfactant is selected from the group comprising of Sorbitan esters, polysorbates, polyether compounds etc.

In yet another embodiment of the present invention it provides a solvent which is selected from the group comprising of ethanol, butanol, ethyl acetate, hexane, carbon dioxide.

In yet another embodiment of the present invention it provides a method of treating or preventing bone disorder by administrating effective amount of formulation.

In yet another embodiment of the present invention it provides a method of prevention and/or treatment of bone related disorders or osteo-health related disorders including fractures, postmenopausal osteoporosis, mitigation of swelling, inflammation, pain and further in regeneration of cartilage useful in the prevention and/or treatment of osteoarthritis.

In an embodiment the formulation is provided in the form of powder or granular formulation of bioactive *spinacia oleracea* that is composed of extract, filler, acid, base, water soluble additive, flavor.

According to another suitable embodiment of the present invention the mixing weight ratio of carrier and extract is preferably 1:1 to 2:1.

According to still another embodiment of present invention sodium hydrogen carbonate is presently contained in an amount of 5-20% based on the total weight of formulation.

According to still another embodiment of present invention, sodium carbonate is preferably contained in an amount 2-10% based on the total weight of formulation.

According to still another embodiment of present invention organic acid is preferably contained in amount of 5-20% based on the total weight of formulation.

One aspect of the present invention provides a solid pharmaceutical dosage form adapted for human consumption. Bio active extract is semisolid, thus not suitable for handling and human consumption. To solve this disadvantage in the present invention extract is thoroughly mixed with a filler, to increase the bulk and flow properties of extract.

The formulation of the present invention is prepared through a method comprising of: Preparing granules by adding filler, acidic and basic components, mixing the granules with other excipients, in case of power formulation the prepared granules are crushed and passed through a sieve.

The filler selected from a group but not limited to cross carmellose sodium, sodium starch glycolate, pregelatinized starch (starch 1500 or Primojel), microcrystalline cellulose, crospovidone, cross-linked povidone and commercially available polyvinylpyrrolidone (PVP, Povidone), low-substituted hydroxypropylcellulose, alginic acid, carboxymethylcellulose, calcium salts and sodium salts, fumed silica (colloidal silica), guar gum, magnesium aluminum silicate, methylcellulose, powdery cellulose, starch and sodium alginate.

Preferably filler may be one or a mixture of two or more selected from the group consisting of crosscarmellose sodium, sodium starch glycolate, pregelatinized starch, microcrystalline cellulose, crosspovidone and commercially available polyvinylpyrrolidone. More preferably, the disintegrant may be crospovidone, sodium starch glycolate or microcrystalline cellulose.

The acid and base components are included in the formulation to improve the dissolution process of the granules or powder. And also to improve the patient acceptability of formulation.

The organic acid according to the present invention may be one or a mixture of two or more selected from the group consisting of citric acid, malic acid, tartaric acid, ascorbic acid, fumaric acid, adipic acid and sodium hydrogen sulfate.

The organic acid and carbonate reacts in presence of aqueous media, to liberate carbon dioxide in few seconds, this facilitate the dissolution of granules and powder. Commonly used carbonates are sodium carbonate, sodium bicarbonate, potassium carbonate, potassium bicarbonate, magnesium carbonate and calcium carbonate. Individual acids and carbonate salts can be used singly or in combination.

The water-soluble additive functions to additionally increase water absorbance in the preparation of oral formulations to increase the initial release rate of the drug and enhances drug absorption in the stomach.

The weight ratio of the water-soluble additive is 0.1-3 wt %, and preferably 0.5-2.5 wt %, based on the total weight of formulation. The water soluble additives may include in the present invention, but are not limited to: sodium lauryl sulfate, sodium lauryl ethoxy sulfates, sodium lauryl sulfoacetate, sodium dodecyl benzene sulfonate, alpha olefin sulfonate, ethylene glycols, propylene glycols, sodium lauryl sulfosuccinate, various fatty alcohols and fatty alcohol ethoxylates, and nonylphenolethoxylates.

According to one aspect of the present invention can further include one or more additional adjuvants and/or active ingredients which can be chosen from those known in the art including diluents, flavors, colors, binders, filler, surfactant, disintegrant, stabilizer, compaction vehicles, and non-effervescent disintegrants, flavors, diluents, colors, binders, filler, surfactant, disintegrant, stabilizer, compaction vehicles, and non-effervescent disintegrants.

Embodiment of the present invention, the effective dose of the formulation is ranging between 125, 250, 500, 750 and 1000 mg. $kg^{-1}$ $day^{-1}$ preferably 1 mg to 750 mg. $kg^{-1}$ $day^{-1}$, daily, bi-weekly, weekly or in more divided doses.

In yet another embodiment of the present invention, the formulation useful for the prevention or treatment of bone disorders may be any diseases and syndromes caused by osteoporosis, bone loss, bone formation, bone fracture healing, attainment of higher peak bone mass when administered during the period of growth, and promotion of new bone formation in vitro/in vivo.

ABBREVIATIONS

A001: Ethanolic extract of *Spinacia oleracea*; C002: Ethanolic extract of dried *Spinacia oleracea* leaves; F004: Fraction of *Spinacia oleracea*; HPLC: High Pressure Liquid Chromatography; LC-MS: Liquid Chromatography Mass Spectrometry; L: Liter; GGT: Gamma-glutamyl transferase; AST: Aspartate aminotransferase; ALT: Alanine aminotransferase; LDH: Lactate dehydrogenase; SDH: Subdural hematoma; GDH: Glutamate Dehydrogenase; ALP: Alkaline phosphatase; HPTLC: High performance thin layer chromatography; NAO: Natural antioxidant mixture; TRAMP: Transgenic Adenocarcinoma Mouse Prostate; $IC_{50}$: Half maximal inhibitory concentration; DPPH: 2,2-diphenyl-1-picrylhydrazyl; NBT: Nitro blue tetrazolium; $CCl_4$: Carbon tetrachloride; SQDG: Sulfoquinovosyl diacylglycerol; DNA: Deoxyribonucleic acid; HL-60: Human promyelocytic leukemia cells; $LD_{50}$: Median lethal dose; ROS: Reactive oxygen species; DOX: Doxorubicin; Ip: Intraperitoneal; UTI: Urinary tract infection, PBM: Peak Bone Mass.

BRIEF DESCRIPTION OF THE DRAWINGS

FIG. 1A-1D: *Spinacea oleracea* extract improves micro-architectural parameters in the drill-hole model for fracture in 14 days. Micro-CT analysis showing bone volume/tissue volume BV/TV (%); trabecular separation (Tb.Sp) (mm), Tb.N, trabecular number (Tb.N)($mm^{-1}$); structure model index SMI. Values are expressed as mean±SEM (n=6 rats/group); *P<0.05, P<0.01, *P<0.001 compared with control group.

FIG. 1E: *Spinacea oleracea* extract accelerates bone regeneration in drill-hole model for fracture as represented by confocal imaging. Figure shows calcein labeling in the callus at the site of drill hole of groups treated with various doses of the extract after 14 days treatment. Increased intensity of the labelling represents greater healing. Images taken at 100×.

FIG. 2A-2D: Formulated *Spinacea oleracea* extract (FSE) showed better micro-architectural response as compared to *Spinacea oleracea* extract alone in drill hole model for fracture. Micro-CT analysis at the fracture site after 14 days of treatment showing BV/TV, bone volume/tissue volume (%); trabecular separation Tb.Sp(mm); trabecular number (Tb.N) ($mm^{-1}$); structure model index (SMI). Values are expressed as mean±SEM (n=8 rats/group); *P<0.05, P<0.01, *P<0.001 compared with control group. #P<0.05, ##P<0.001, ###P<0.0001 compared to extract.

FIG. 2E: Formulated *Spinacea oleracea* extract accelerates bone regeneration in drill-hole model for fracture as represented by confocal imaging. Figure shows calcein labeling in the callus at the site of drill hole of groups treated with various doses of the extract after 14 days treatment. Increased intensity of the labelling represents greater healing. Images taken at 100×.

FIG. 2F: Graph represents quantification of mean intensity of calcein label per pixel. All values are expressed as mean±SEM n=4; *p<0.05, p<0.01, *p<0.001 compared to control. #p<0.05 compared to extract.

FIG. 2G-2I: qPCR determination of mRNA level of osteogenic genes BMP-2, COL 1 and BMP4 from the fracture site of various groups. Each assay was performed in triplicate and results are represented as mean±SEM; *p<0.05, p<0.01, *p<0.001 compared to control and #p<0.05, ##p<0.01. compared to *spinacea* extract.

FIG. 3: *Spinacea oleracea* extract is not estrogenic in the uterus. Uterine weight was measured at the end of treatment period of 3 months in ovariectomised rats. Data show mean±S.D. ***p<0.001 compared to ovariectomised group. The uterine weight is equivalent in OVx and OVx+treatment groups at both the doses (750 mg·$kg^{-1}$$dy^{-1}$ and 1000 mg·$kg^{-1}$$dy^{-1}$).

FIG. 6A-6E: *Spinacea oleracea* extract (2492) ameliorates monosodium iodoacetate (MIA) induced osteoarthritis in SD rats. Gross morphological images of knee and microarchitectural parameters as assessed by micro-CT showed the protective effect of *Spinacea oleracea* extract on MIA induced osteoarthritis.

DETAILED DESCRIPTION OF THE INVENTION

Figure 1F:
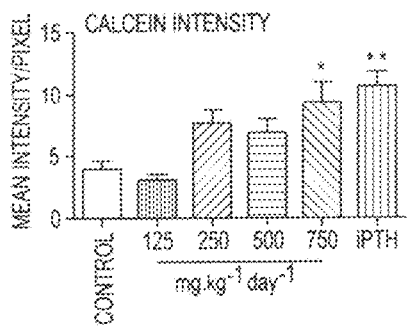
FIG. 1F: Quantification of mean intensity of calcein label per pixel at fracture site of various groups treated with extract. All values are expressed as mean±SEM n=4; p<0.05, p<0.01, *p<0.001 compared to control
Figure 1G:
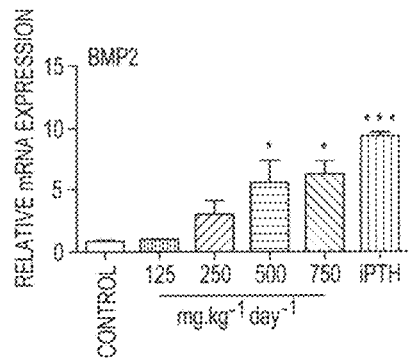
FIG. 1G-1I: qPCR determination of mRNA levels of osteogenic genes at the site of fracture. Expression of BMP-2, Col-1 and BMP4 was assessed at site of injury in various groups. Values represent mean±SEM *P<0.05, P<0.01, *P<0.001 compared to vehicle treated control group.
Figure 1H:
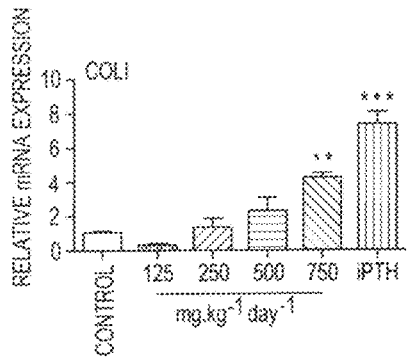
Figure 1I:
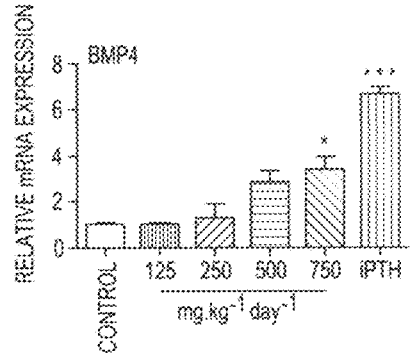
Figure 2A:
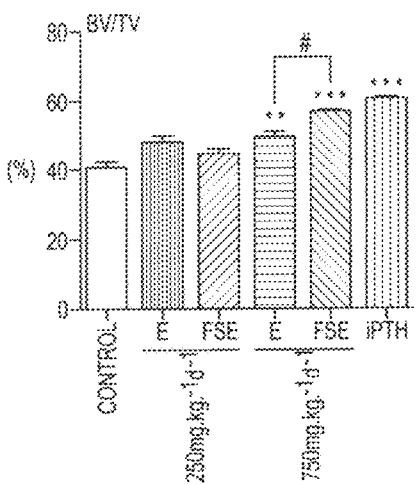
Figure 2B:
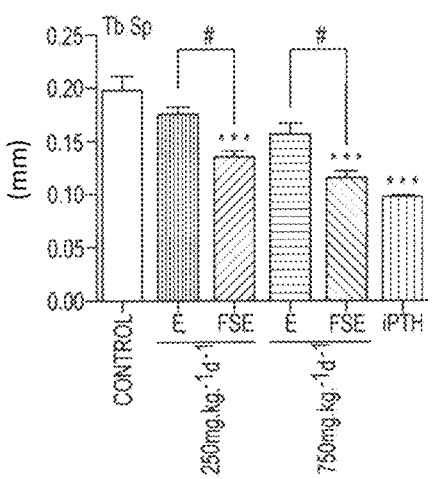
Figure 4A:
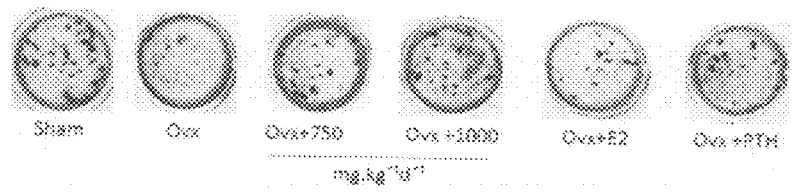
FIG. 4A-4B: Treatment with *Spinacea oleracea* extract increased mineralized nodule formation in bone marrow cells (BMCs) as assessed by Alizarin red-S staining in ex-vivo cultures. Values represent Mean±SEM of three independent experiments n=3. *P<0.05, **P<0.01 as compared with OVx+vehicle group.
Figure 4B:
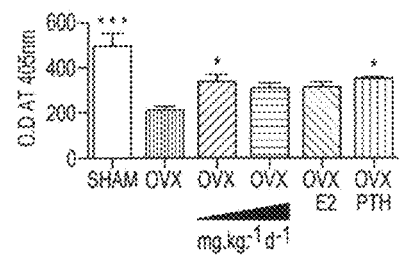
Figure 5A:
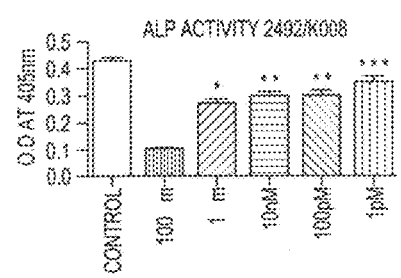
FIG. 5A-5C: Activity of the compound C003/K008 isolated from the extract was assessed by measuring ALP activity in calvarial osteoblast cells. At the end of the experiment, ALP activity was measured colorimetrically. Data shows mean±SEM. (*p<0.05, p<0.01 and *p<0.001 when compared with control). Calvarial osteoblasts were treated with compound C003/K008 at various concentration for 18 days to induce mineralization. At the end of the experiments, cells were stained with Alizarin Red-S. Photomicrographs show increased formation of mineralized nodules by compound 2492/K008 treatment compared to control (untreated cells). Bar diagram in the lower panel shows quantification of mineralization by extraction of Alizarin Red-S dye. Values are expressed as mean±SEM. ***p<0.001 and *p<0.05 when compared with control (untreated cells).
Figure 5B:
Figure 5C:
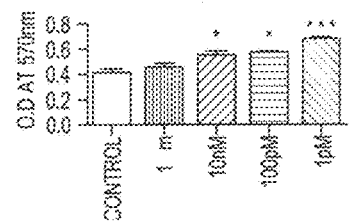
Figure 6F:
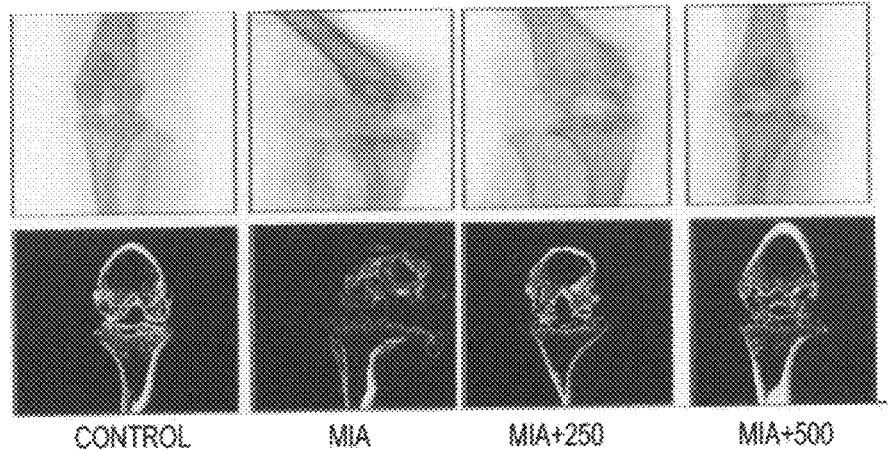
FIG. 6F: X-ray and micro-CT 2D images of joints from different groups demonstrating the antagonizing effect of *Spinacea oleracea* extract on MIA induced osteoarthritis.
Figure 6G:
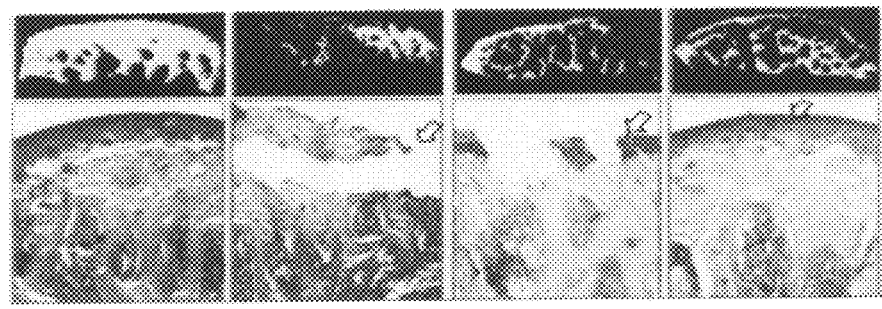
FIG. 6G: Histological images showing the chondroprotective effect and regeneration of cartilage at 500 mg·kg$^{-1}$ dose of the extract.
Figure 6H:
FIG. 6H: Micro-CT images showing protective effect on trabecular bone in MIA induced animals at 250 and 500 mg·kg$^{-1}$ dose of the extract.
Figure 7:
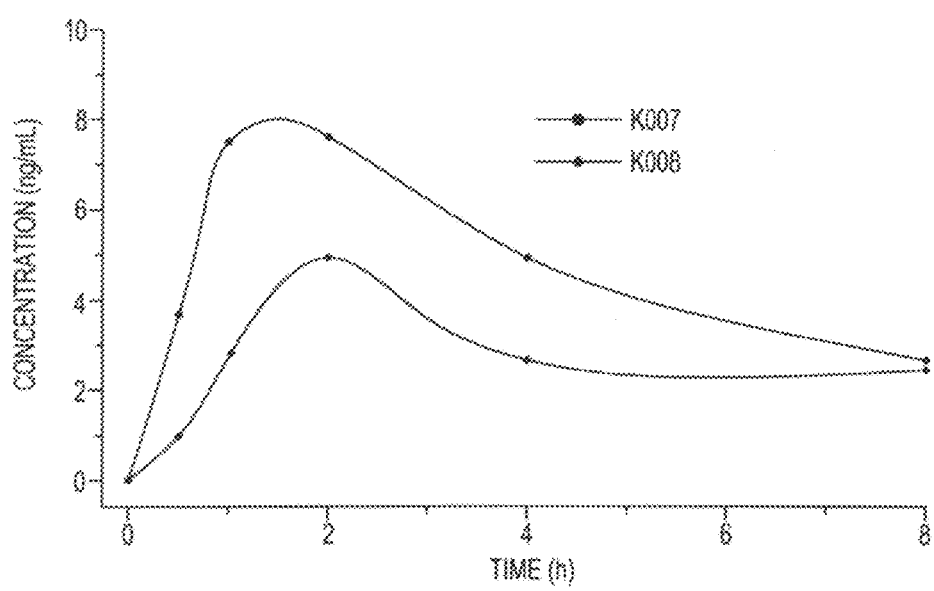
FIG. 7: Pharmacokinetic parameters of K007 and K008 after oral dosing of 250 mg·kg$^{-1}$ formulation of the extract in male Sprague Dawley rats.

Embodiment of the present invention, the effective dose of the pharmaceutical formulation is ranging between 125, 250, 500, 750 and 1000 mg. kg$^{-1}$ day$^{-1}$ preferably 250 mg to 750 mg. kg$^{-1}$ day$^{-1}$, daily, bi-weekly, weekly or in more divided doses.

In yet another embodiment of the present invention, the pharmaceutical formulation is useful for the prevention or treatment of bone disorders may be any diseases and syndromes caused by osteoporosis, bone loss, bone formation, bone fracture healing, attainment of higher peak bone mass when administered during the period of growth, and promotion of new bone formation in vitro/in vivo.

In an embodiment the formulation is provided in the form of powder or granular formulation of bioactive *spinacia oleracea* that is composed of extract, filler, acid, base, water soluble additive, flavor.

According to still another embodiment of present invention organic acid is preferably contained in amount of 5-20% based on the total weight of formulation.

One aspect of the present invention provides a solid pharmaceutical dosage form adapted for human consumption. Bio-active extract is semisolid, thus not suitable for handling and human consumption. To solve this disadvantages in the present invention extract is thoroughly mixed with a filler, to increase the bulk and flow properties of extract.

The acid and base components are included in the formulation to improve the dissolution process of the granules or powder. And also to improve the patient acceptability of formulation.

The organic acid according to the present invention may be one or a mixture of two or more selected from the group consisting of citric acid, malic acid, tartaric acid, ascorbic acid, fumaric acid, adipic acid and sodium hydrogen sulfate.

The organic acid and carbonate reacts in presence of aqueous media, to liberate carbon dioxide in few seconds, this facilitate the dissolution of granules and powder. Commonly used carbonates are sodium carbonate, sodium bicarbonate, potassium carbonate, potassium bicarbonate, magnesium carbonate and calcium carbonate. Individual acids and carbonate salts can be used singly or in combination.

The water-soluble additive functions to additionally increase water absorbance in the preparation of oral formulations to increase the initial release rate of the drug and enhances drug absorption in the stomach.

The weight ratio of the water-soluble additive is 0.1-10 wt %, and preferably 1-6 wt %, based on the total weight of formulation. The water soluble additives may include in the present invention, but are not limited to: sodium lauryl sulfate, sodium lauryl ethoxy sulfates, sodium lauryl sulfoacetate, sodium dodecyl benzene sulfonate, alpha olefin sulfonate, ethylene glycols, propylene glycols, sodium lauryl sulfosuccinate, various fatty alcohols and fatty alcohol ethoxylates, and nonylphenolethoxylates.

According to one aspect of the present invention can further include one or more additional adjuvants and/or active ingredients which can be chosen from those known in the art including diluents, flavors, colors, binders, filler, surfactant, disintegrant, stabilizer, compaction vehicles, and non-effervescent disintegrants. flavors, diluents, colors, binders, filler, surfactant, disintegrant, stabilizer, compaction vehicles, and non-effervescent disintegrants.

In another embodiment the invention provides a process wherein the surfactant mix is prepared by mixing surfactant (15% to 35% w/w) and co-surfactant (10 to 25% w/w).

In another embodiment the invention provides a formulation wherein said formulation protects the said disorders at a dose ranging between 250 and 750 mg·kg-1·day-1., wherein the fraction protects the disorders at a dose ranging between 25 to 200 mg·kg-1·day-1.

In another embodiment the invention provides use of the pharmaceutical formulation for prevention and/or treatment of bone related disorders or osteo-health related disorders including fractures, postmenopausal osteoporosis, mitigation of swelling, inflammation, pain and further in regeneration of cartilage useful in the prevention and/or treatment of osteoarthritis.

Methods of preventing or treating disorders or disease conditions mentioned herein comprise administering to an individual human being or any other mammal or any other animal in need of such treatment a therapeutically effective amount of one or more of the agents of this invention.

Such doses may be administered by any appropriate route for example, oral, systemic, local or topical delivery for example, intravenous, intra-arterial, intra-muscular, subcutaneous, intraperitoneal, intra-dermal, buccal, intranasal, inhalation, vaginal, rectal, transdermal or any other suitable means in any conventional liquid or solid dosage form to achieve, conventional delivery, controlled delivery or targeted delivery of the compounds of this invention or a pharmaceutically acceptable salt or a pharmaceutically acceptable formulation thereof with one or more of the pharmaceutically acceptable carriers, excipients etc.

A preferred mode of administration of agents of the present invention or a pharmaceutically acceptable salt or a pharmaceutically acceptable formulation thereof is oral. Oral compositions will generally comprise of agents of the present invention or a pharmaceutically acceptable formulation thereof and one or more of the pharmaceutically acceptable excipients.

The oral compositions such as tablets, pills, capsules, powders, granules, and the likes may contain any of the following pharmaceutically acceptable excipients:
1. a surfactant/co-surfactant selected from the group comprising of Sorbitan esters, polysorbates, polyether compounds etc.
2. a formulation wherein pharmaceutically acceptable additives is selected from the group comprising of microcrystalline cellulose, crospovidone, cross-linked povidone and commercially available polyvinylpyrrolidone (PVP, Povidone), low-substituted hydroxypropylcellulose, alginic acid, carboxymethylcellulose, calcium salts and sodium salts, fumed silica (colloidal silica), guar gum, magnesium aluminum silicate, methylcellulose, powdery cellulose, starch and sodium alginate etc.
3. a sweetening agent such as sucrose, saccharin or any other ingredient of the similar nature alone or in a suitable combination thereof;
4. a flavoring agent such as peppermint, methyl salicylate, orange flavor, vanilla flavor, or any other pharmaceutically acceptable flavor alone or in a suitable combination thereof;
5. wetting agents such as cetyl alcohol, glyceryl monostearate or any other pharmaceutically acceptable flavor alone or in a suitable combination thereof;
6. absorbents such as kaolin, bentonite clay or any other pharmaceutically acceptable flavor alone or in a suitable combination thereof;
7. solution retarding agents such as wax, paraffin or any other pharmaceutically acceptable flavor alone or in a suitable combination thereof.

Therefore, the present invention seeks to overcome prior problems associated with the cure and the management associated with estrogen dependent or independent diseases or syndromes or disorders preferably in the prevention or treatment of estrogen dependent or independent diseases caused in humans and animals and more particularly the bone health disorders and syndromes. The invention also seeks to promote peak bone mass achievement during skeletal growth as occurs in adolescence. The invention also discloses the treatment of conditions associated with cartilage like osteoarthritis. The n-ethanol soluble fraction from Spinacea oleracea described in the present invention are useful in the management, prevention treatment, and cure of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals.

Accordingly the present invention provides a n-ethanol and butanol soluble fraction from leaves derived from Spinacea oleracea in pharmaceutically acceptable form to enhance their application potential for the management or prevention or treatment or cure of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals, by the process and the methods described in the present invention.

EXAMPLES

The following examples, which include preferred embodiments, will serve to illustrate the practice of this invention; it being understood that the particulars shown by way of example and for purpose of illustrative discussion of preferred embodiments of the invention.

The plant extracts and isolated pure compounds thereof were evaluated for the use of estrogen dependent or independent diseases or syndromes or diseases preferably in the prevention or treatment of estrogen dependent or independent diseases or syndromes or diseases caused in humans and animals, and achievement of PBM during skeletal growth and health in mammals.

The activity testing illustrated in the following examples should, however, not be construed to limit the scope of invention.

Specifications of Raw Materials Used in the Extraction Process

Spinacia oleracea Linn. is cultivated throughout India, commonly known as "Palak" in Hindi, Spinacia oleracea (CDRI plant code No. 2492) was purchased from local market of Lucknow-226021, located at 26.8° N 80.9° E in U.P. India.

Example 1: Extraction with Ethanol of Spinacia oleracea Leaf Extract (SE)

The Spinacia oleracea leaves (CDRI plant code No. 2492, 30 kg) was cut into small pieces and placed in glass percolator with ethanol (20 L) and is allowed to stand at room temperature for about 24 hours. The percolate was collected. This process of extraction was repeated for four times. The combined extract was filtered, concentrated under reduced pressure at 45° C., weight of extract obtained 560 g (1.8%, 2492-C002).

Example 2: For Extraction of Dried Spinacia oleracea Leaf Extract with Ethanol (DSE)

The Spinacia oleracea leaves were dried in the shade in a well ventilated enclosure. The dried leaves were powdered (3 kg) and placed in glass percolator with ethanol (5 L) and are allowed to stand at room temperature for about 24 hours. The percolate was collected. This process of extraction was repeated for four times. The combined extract was filtered, concentrated under reduced pressure at 45° C., weight of extract obtained 540 g (18%, 2492-C003). This forms the 'Stock Extract' of dried Spinacia oleracea leaves, stored at 4° C.

Example 3

For Fractionation of Aqueous ethanolic extract (270 g, 2492-C002).) was triturated with ethyl acetate (500 ml×8). The ethyl acetate soluble fraction was then concentrated under the reduced pressure at 40° C., weight of ethyl acetate fraction obtained 34.0 g (12.59%, with respect to extract, F004). The insoluble residue was suspended in water (1000 ml), extracted with n-butanol saturated with water ((800 ml×7) ml). The combined n-butanol soluble fraction was concentrated under the reduced pressure at 45° C., weight of n-butanol soluble fraction 112.0 g (41.48%, with respect to extract, F005). The aqueous fraction obtained was 115 g (42.59% with respect to extract, F006).

Example 4: Isolation of Compounds from n-Butanol Soluble Fraction (2492, F005) of *Spinacia oleracea* Leaves The n-BuOH soluble fraction (95.0 g, F005) was subjected to silica gel column chromatography (100-200 mesh), with the ethyl actate and gradient of EtOAc-MeOH (95:5, 90:10, 75:25, 65:35, 50:50 and MeOH) as eluent. Six fractions (f1-f6) were collected according to TLC analysis. Fraction F2 was purified on silica gel column chromatography eluted with $CHCl_3$-MeOH (97:03) afforded 50 mg of Compound I, K007 (0.0525% w/w with respect to extract) while etution with $CHCl_3$-MeOH (95:05) afforded 20 mg of Compound II, K008 (0.021% with respect to extract). These compounds were characterized from detailed spectroscopic studies.

Compound (2492/K008) was isolated from butanolic fraction and alkaline phosphatase activity and mineralization in calvarial osteoblast cells assessed with different concentrations of the test compound or vehicle for 48 hrs in growth medium supplemented with 10 mM β-glycerophosphate and 50 µg/ml ascorbic acid. At the end of incubation period, cells were washed with PBS and kept in −80° C. for 30 min and then at 37° C. for 30 min. ALP activity was measured using p-nitrophenylphosphate (PNPP) as substrate and absorbance was read at 405 nm. SE increased the alkaline phosphatase activity from doses ranging from 1 µM to 1 µM as compared to the control with ~2.0 fold increase in the ALP activity at 1 µM.

Example 5: Finger Printing of *Spinacia oleracea* Extract Using HPLC

Finger printing of *spinacea* extract (2492 C003; 2492 F005; K007 and K008 was carried out using HPLC. The HPLC was carried out on Shimadzu HPLC system (LC solutions ver 1.25) using mobile phase with composition: 0.2% v/v phosphoric acid in water: methanol in a ratio of 48:54. The compounds were detected at 365 nm at flow rate of 1.0 ml/min.

Example 6: Characterization of Isolated Compounds i. 5,3',4'-trihydroxy-3-methoxy-6,7-methylenedioxy-flavone (2492/K007): Light yellow solid; ESIMS: m/z 345 $[M+1]^+$; $C_{17}H_{12}O_8$; $^1H$ NMR: (DMSO-$d_6$, 400 MHz) δ: 6.88 (1H, s, H-8), 7.57 (1H, d, J=2.1 Hz, H-2'), 6.91 (1H, d, J=8.0 Hz, H-5'), 7.45 (1H, dd, J=8.4, 2.1 Hz, H-6'), 6.16 (2H, s, methelene dioxy), 3.80 (3H, s, $OCH_3$), 12.70 (1H, s, 5-OH); $^{13}C$ NMR: (DMSO-$d_6$, 100 MHz) δ: 178.41 (C-4), 156.04 (C-2), 153.86 (C-7), 151.66 (C-8a), 148.82 (C-4'), 145.25 (C-3'), 140.50 (C-5), 137.66 (C-3), 129.16 (C-6), 120.62 (C-1'), 120.55 (C-6'), 115.70 (C-5'), 115.48 (C-2'), 107.11 (C-4a), 102.77 (methelene dioxy), 89.46 (C-5), 59.61 ($OCH_3$)

ii. 5,7,3',4'-tetrahydroxy-3,6-dimethoxy-flavone (2492/K008):Light yellow solid; ESIMS: m/z 347 $[M+1]^+$; $C_{17}H_{14}O_8$; $^1H$ NMR: ($CD_3OD$, 400 MHz) δ: 6.51 (1H, s, H-8), 7.64 (1H, d, J=2.1 Hz, H-2'), 6.90 (1H, d, J=8.5 Hz, H-5'), 7.55 (1H, dd, J=8.5, 2.1 Hz, H-6'), 3.89 (3H, s, $OCH_3$), 3.80 (3H, s, $OCH_3$). $^{13}C$ NMR: ($CD_3OD$, 100 MHz) δ: 180.3 (C-4), 158.8 (C-7), 158.1 (C-2), 153.8 (C-8a), 153.7 (C-5), 150.0 (C-4'), 146.5 (C-3'), 139.1 (C-3), 132.6 (C-6), 123.1 (C-1'), 122.0 (C-6'), 116.1 (C-2'), 115.9 (C-5'), 107.6 (C-4a), 95.0 (C-8), 61.0 (6-OMe), 60.1 (3-OMe).

Example 7: Development of SMEDDS Formulation for Dried *Spinacea* Extract (DSE)

The formulation was prepared by dissolving weighed quantity of *Spinacia oleracea* extract (8% W/W) in the mixture of oleic acid (50% W/W), tween 80 (18% W/W), propylene glycol (18% W/W), PEG 600 (6% W/W). This mixture was kept on stirring at 70° C. over night to obtain a clear and transparent preparation. This formulation was stored at ambient temperature for further use.

Example 8

The formulation was prepared by dissolving weighed quantity of *Spinacia oleracea* extract (5% W/W) in the mixture of oleic acid (52% W/W), tween 80 (20% W/W), propylene glycol (20% W/W), PEG 600 (7% W/W). This mixture was kept on stirring at 70° C. over night to obtain a clear and transparent preparation. This formulation was stored at ambient temperature for further use.

Example 9

The formulation was prepared by dissolving weighed quantity of *Spinacia oleracea* extract (2.5% W/W) in the mixture of oleic acid (60% W/W), tween 80 (16% W/W), propylene glycol (15% W/W), PEG 600 (8% W/W). This mixture was kept on stirring at 65° C. over night to obtain a clear and transparent preparation. This formulation was stored at ambient temperature for further use.

Example 10

The formulation was prepared by dissolving weighed quantity of *Spinacia oleracea* extract (5% W/W) in the mixture of oleic acid (48% W/W), tween 80 (20% W/W), propylene glycol (16% W/W), PEG 600 (8% W/W). This mixture was kept on stirring at 65° C. over night to obtain a clear and transparent preparation. This formulation was stored at ambient temperature for further use.

Biological Evaluation

The plant extracts was evaluated for the use in fracture healing model and for estrogen dependent or independent diseases or syndromes or diseases preferably in the prevention or treatment of estrogen dependent or independent diseases or syndromes or diseases caused in humans and animals, and achievement of PBM during skeletal growth and health in mammals. The activity testing illustrated in the following examples should, however, not be construed to limit the scope of invention.

Example 11: Animal Studies on Drill Hole Model for Fracture

A standardized fraction (2492) obtained from a an annual and edible flowering plant (code 2492) was found to have osteoprotective and bone anabolic effects in a WHO approved model for postmenopausal osteopenia (adult Sprague Dawley rats in drill hole model for fracture healing and bilateral ovariectomy (OVx)] model for primary osteoporosis. The study was conducted in accordance with current legislation on animal experiments [Institutional Animal Ethical Committee (IAEC)] at C.D.R.I. All rats were individually housed at 21° C., in 12-h light: 12-h dark cycles. Adult female Sprague Dawley rats weighing ~160-180 gm were randomly divided into 6 groups comprising of 8 animals in each group to receive 125 mg·Kg$^{-1}$, 250 mg·Kg$^{-1}$, 500 mg·Kg$^{-1}$, 750 mg·Kg$^{-1}$, iPTH (30 µg·Kg$^{-1}$ intermittently) and vehicle. Drill-hole injury was created in the mid femur region 1 cm above the knee joint by inserting a drill hole of diameter 0.8 mm in the anterior portion of the diaphysis of the bilateral femurs. Treatment was started next day of injury and continued for 14 days. Each animal received intraperitoneal administration of fluorochrome calcein(20 mg/kg) 24 h before autopsy. After 14 days of treatment, animals were sacrificed and autopsied to collect their femurs for the measurement of bone micro-architectural parameters. Bones were embedded inacrylic material and 50-mm sections were made using an Isomet BoneCutter (Buehler, Lake Bluff, Ill., USA) and photographs taken under confocal microscope LSM 510 Meta, Carl Zeiss, Maple Grove, Minn., USA) aided with appropriate filters. The intensity of calcein binding, was calculated using Carl Zeiss AM 4.2 image-analysis software.

Example 12: Effect of *Spinacea* Extract (SE) on Bone Regeneration (A) In vivo regeneration of bone to monitor local repair process was done using micro-CT after creation of the hole using on femur of 0.8 mm diameter. Vehicle treated group displayed lower BV/TV compared to the extract 2492/C002 and iPTH treated group after 14 days of treatment. Significant increase ~24.8% in bone volume is to tissue volume (BV/TV), trabecular Number (Tb.No.) 24.3% with decrease in trabecular separation (Tb.Sp.) 25.4% and structural model index (SMI) 46.2% was observed at 750 mg·Kg$^{-1}$day$^{-1}$ as compared to the control group. Data was comparable to standard iPTH group. However, no significant changes were observed in these parameters at lower doses (250 mg·Kg$^{-1}$, 500 mg·Kg$^{-1}$) of the extract and when compared to 750 mg dose or the standard control in PTH treated group. (B) As a part of calcein labeling intensity of in the drill hole shows that *Spinacea* Extract at 750 mg/kg/day increased mineral deposition as early as 14 days. Modest mineralized calluses appeared at defect and intra-medulla region of treated groups. By day 14, extent of callus mineralization increased, in the intra-medulla region. Post drilling on 14th day, extract treatment with 250, 500 and 750 mg/kg/day dose led to fracture repair but predominantly occupied mineralized callus was observed with 750 mg·kg$^{-1}$·day$^{-1}$, and defect region was bridged by day 14, however maximum mineralized callus within intra-medulla region was observed in iPTH treated animals and the injury was healed to a greater extent. (c) The results of osteogenic genes were consistent with Q-PCR data with increased expression of osteogenic genes BMP2, BMP4 and COL1 mRNA. Expression of genes peaked significantly after 14 days of treatment with extract in comparison to vehicle treated animals. Comparison amongst doses revealed that 750 mg·kg$^{-1}$·day$^{-1}$ was the most effective in stimulating the osteogenic genes.

Example 13: Creating a Drill Hole Model for Fracture to Study the Effect of Formulated *Spinacea* Extract (FSE)

The model was made as described above and then treatment of extract and Formulated *Spinacea* Extraxt (FSE) was started at doses of 250 and 750 mg·kg$^{-1}$·day$^{-1}$ from the next day of injury and continued for 14 days. After 14 days of treatment as described above, animals were sacrificed and autopsied to collect their femurs for the measurement of bonemicro architectural parameters at the drill-hole site. Bones were embedded inacrylic material and 50-mm sections were made using an Isomet BoneCutter (Buehler, Lake Bluff, Ill., USA) and photographs taken under confocal microscope LSM 510 Meta, Carl Zeiss, Maple Grove, Minn., USA) aided with appropriate filters. The intensity of calcein binding, which is an indicator of the amount of new mineral deposition, was calculated using Carl Zeiss AM 4.2 image-analysis software.

Example 14: Effect of Formulated *Spinacea* Extract (FSE) 2492/C002 on Bone Regeneration (A) In vivo regeneration of bone to monitor local repair process was done using micro-CT after creation of the hole using on femur of 0.8 mm diameter. Vehicle treated group displayed lower BV/TV compared to the extract SE and iPTH treated group after 14 days of treatment. At a dose of 750 mg·Kg$^{-1}$ FSE exhibited significant increase ~12.9% in BV/TV, 48.3% Tb.No. with decrease in Tb.Sp. of ~25.6% and SMI of 52.7% as compared to the non formulated 750 mg·Kg$^{-1}$day$^{-1}$ dose Data of FSE was comparable to the iPTH group. However, no significant changes were observed in these parameters at lower dose of formulated 250 mg·Kg$^{-1}$ group when compared to 750 mg dose or the standard control in PTH treated group. Overall, data suggests that formulating 750 mg·Kg$^{-1}$day$^{-1}$ dose was effective in treating injury at the drill hole site with better efficacy as compared to the not formulated 750 mg·Kg$^{-1}$day$^{-1}$ dose. (B) The results of osteogenic genes were consistent with Q-PCR data with increased expression of osteogenic genes BMP2, BMP4 and COL1 mRNA. Expression of genes peaked significantly after 14 days of treatment with extract in comparison to vehicle treated animals. Comparison amongst doses revealed that 750 mg·kg$^{-1}$·day$^{-1}$ was the most effective in stimulating the osteogenic genes.

Example 15: Effect of Dried *Spinacea* Extract (DSE) 2492/C003 on Bone Regeneration In vivo regeneration of bone to monitor local repair process was done using micro-CT after creation of the hole using on femur of 0.8 mm diameter. Treatment with DSE after fracture creation was given at three doses of 250 mg·Kg$^{-1}$, 500 mg·Kg$^{-1}$, 750 mg·Kg$^{-1}$.

Vehicle treated group displayed lower BV/TV as compared to 2492/C003 after 14 days of treatment. Significant increase in bone volume is to tissue volume (BV/TV) ~25.6%, trabecular Number (Tb.No.) 33.3% with a decrease in trabecular separation (Tb.Sp.) 32.8% and structural model index (SMI) 38.4% was observed in 500 mg·Kg$^{-1}$day$^{-1}$. We observed compared data with 750 mg·Kg$^{-1}$day$^{-1}$. Data shows that even a lower dose of 500 mg·Kg$^{-1}$day$^{-1}$ of DSE was effective as compared to either *spinacea* extract (SE) or formulated *spinacea* extract (FSE) where the effective dose was 750 mg·Kg$^{-1}$day$^{-1}$.

Example 16: Effect of Formulated Dried *Spinacea* Extract (FDSE) 2492/C003 on Bone Regeneration In vivo regeneration of bone to monitor local repair process was done using micro-CT after creation of the hole using on femur of 0.8 mm diameter. Treatment with DSE and formulated DSE after fracture creation was given at three doses of 250 mg·Kg$^{-1}$, 500 mg·Kg$^{-1}$, 750 mg·Kg$^{-1}$. Vehicle treated group displayed lower BV/TV as compared to 2492/C003 and its formulation after 14 days of treatment. However, formulated DSE showed significant enhancement in bone volume is to tissue volume (BV/TV) as compared to unformulated 2492/C003(DSE). Formulation dried *spinacea* extract resulted in approximately 50% reduction in the dose as compared to unformulated DSE. Data shows that even a lower dose of 250 mg·Kg$^{-1}$day$^{-1}$ of FDSE was effective as compared to either dried *spinacea* extract (DSE).

Example 17: Treatment of Ethanol Fraction of *Spinacea* Extract (SE) in Ovariectomized Sprague Dawley Rats The study was conducted in accordance with current legislation on animal experiments [Institutional Animal Ethical Committee (IAEC)] at C.D.R.I. Immature Sprague Dawley rats weighing ~180-200 gm were either bilaterally ovariectomized (OVx) or exposed to a sham surgical procedure. All rats were individually housed at 21° C., in 12-h light:12-h dark cycles. All rats had excess to normal chow diet and water ad libitum. After OVx, the rats were left for 12 weeks to develop osteopenia. After 12 weeks, extract treatment in the form of gavage (50.0 mg and 100 mg/kg body weight), and iPTH 30 μg·kg$^{-1}$ three times a week was given daily. Equal numbers of OVx and sham operated rats served as the control, and were given vehicle (20% ethanol). The rats were weighed each week. At the end of 12 weeks, urine was to be collected for biochemical assessment therefore the rats were caged individually in plastic cages fitted with steel mesh for a total period of 48 h preceding autopsy and had free access to normal chow diet and water for the first 24 h initially for of acclimatization and then during the next 24 h, animals received only water ad libitum. After twenty-four hours of fasting urine samples were collected in fresh containers, centrifuged at 2000 rpm at room temperature and stored at 20° C. until analyzed. Rats were then euthanized. At autopsy, blood samples were collected by cardiac puncture in tubes. Uteri were carefully excised, gently blotted, weighed, and fixed for histology and histomorphometry. About 5 mm pieces from the middle segment of each uterus were dehydrated in ascending grades of ethanol, cleared in xylene, and embedded in paraffin wax using standard procedures. Photomicrographs of sections were obtained using a Leica DC 300 camera and Leica IM50 Image Acquisition software fitted to a Leica DMLB microscope. Histomorphometric measurements were done using Leica Qwin-Semiautomatic image Analysis software. μCT (both 2-D and 3-D) determination of excised bones was carried out using the Sky Scan 1076 μCT scanner (Aartselaar, Belgium) using the cone-beam reconstruction software version 2.6 based on the Feldkamp algorithm (Skyscan).

Example 18: Evaluation of Trabecular Microarchitecture and Uterine Weight

Trabecular response to FSE treatment of OVx rats was quantified at the femur epiphysis. Femoral data show (table below) that compared with the sham group, the OVx+ vehicle group had reduced BV/TV, Tb.No and Tb.Th, and increased Tb.sp and SMI. Comparison of FSE treatment group with the OVx+vehicle group revealed significant increase in BV/TV and Tb.Th., and decrease in Tb.sp and SMI, suggesting that the microarchitectural features of the femoral trabecular bones are significantly protected by SE treatment of OVx rats. Efficacy of OVx was confirmed by studying uterine weight. *Spinach oleracea* extract was generally well tolerated for the duration (12 wk) of administration. OVx group had reduced uterine weight as compared with the ovary intact, sham group. Uterine weight of SE treatment groups (750 mg·kg$^{-1}$dy$^{-1}$ and 1000 mg·kg$^{-1}$dy$^{-1}$ doses) and OVx+PTH remained equivalent to OVx group. E2 increased uterine weight in OVx rats equal to the sham group.

TABLE 1

Changes in trabecular microarchiecture of femur and uterine weight

| Trabecular parameter | Sham | Ovx | Ovx + 750 mgkg$^{-1}$ day$^{-1}$ | Ovx + 1000 mgkg$^{-1}$ day$^{-1}$ | Ovx + E2 (0.1 mgkg$^{-1}$day$^{-1}$) | Ovx + PTH (30 μg/kg bw) |
|---|---|---|---|---|---|---|
| BV/TV (%) | 26.39 ± 1.11*** | 7.39 ± 1.37 | 16.4 ± 1.15*** | 12.29 ± 0.96* | 15.97 ± 1.88*** | 22.78 ± 1.76*** |
| Tb.Sp (mm) | 0.58 ± 0.08*** | 1.11 ± 0.08 | 0.79 ± 0.05** | 0.84 ± 0.05** | 0.76 ± 0.1** | 0.63 ± 0.07*** |
| Tb.No (mm$^{-1}$) | 2.92 ± 0.13*** | 0.69 ± 0.13 | 1.32 ± 0.1* | 1.28 ± 0.11* | 1.61 ± 0.23** | 2.43 ± 0.19*** |
| Tb.Pf | 2.88 ± 0.48*** | 10.86 ± 1.4 | 6.43 ± 1.10** | 6.45 ± 0.65** | 6.22 ± 0.72** | 5.31 ± 0.68*** |
| SMI | 1.35 ± 0.05*** | 2.06 ± 0.12 | 1.72 ± 0.07* | 1.70 ± 0.06* | 1.67 ± 0.04* | 1.26 ± 0.18*** |
| Po (tot) (%) | 73.61 ± 1.12*** | 92.60 ± 1.37 | 85.60 ± 1.96* | 87.76 ± 0.98 | 85.24 ± 2.07 | 76.79 ± 2.35*** |
| Uteriewt (mg) | 415.65 ± 22.71*** | 81.07 ± 4.85 | 98.73 ± 7.05 | 105.4 ± 6.94 | 329.63 ± 30.44*** | 91.18 ± 3.84 |

*Spinacea* extract restores the trabecular micro-architecture of the femur epiphysis after ovariectomy as represented by micro CT data.
Parameters include Bone volume/Tissue volume (BV/TV), Trabecular Spacing (Tb.Sp), Trabecular Number (Tb.N), Trabecular pattern factor (Tb.pf) Structure Model index (SMI), Total porosity percent Po (tot).
Values represent mean ± SEM;
n = 8 rats/group.
***P < 0.001,
**P < 0.01,
*P < 0.05 compared to OVx + veh group.

Example 19: Bone Formation Parameters Upon Oral Administration of DSE, FDSE (Ethanolic Extract) and DSE, FDSE (Butanolic Fraction) in Fracture Healing at Two Different Doses and its Comparison with PTH (s.c Injection)

Trabecular response to DSE and FDSE (ethanolic extract) treatment in drill hole model for fracture healing has been shown in Table below. Data shows that bone volume to tissue volume (BV/TV) increased from 36.44 to 51.64% on treatment with DSE and FDSE (ethanolic extract) at 250 mg–1.d–1. Moreover, when DSE (butanolic fraction) was taken we observed further increase in (BV/TV) as compared to DSE (ethanolic extract). Further, FDSE (butanolic fraction), a formulation, when administered at equivalent dose the BV/TV was increased from 60.66 to 69.23% as compared to the unformulated DSE (butanolic fraction). Data of formulated butanolic fraction (FDSE) was better than the standard marketed drug PTH.

revealed smooth and shiny articular surfaces. The knees of the MIA-treated group showed irregular abrasions at the

TABLE 2

Quantitative estimation of bone formation parameters upon oral administration of DSE, FDSE (ethanolic extract) and DSE, FDSE (butanolic fraction) in fracture healing at two different doses and its comparison with PTH (s.c injection)

| Femur | Control | DSE 250 (EE) mg·kg$^{-1}$ day$^{-1}$ | FDSE 250 (EE) mg·kg$^{-1}$ day$^{-1}$ | DSE 250 (BF; F004) mg·kg$^{-1}$ day$^{-1}$ | FDSE 250 (BF; F004) mg·kg$^{-1}$ day$^{-1}$ |
|---|---|---|---|---|---|
| BV/TV (%) | 41.03 ± 2.5 | 36.44 ± 2.62 | 51.64 ± 1.94**### | 60.66 ± 4.34*** | 69.23 ± 3.88*** |
| SMI (Index) | 1.37 ± 0.2 | 1.0 ± 0.09 | 0.54 ± 0.07***# | 0.82 ± 0.04*** | 0.71 ± 0.06*** |
| Calcein intensity (%) | 8.44 ± 0.3 | 8.97 ± 0.85 | 15 ± 0.78***### | 19.73 ± 3.15*** | 25.18 ± 2.72*** |

| Femur | | DSE 500 mg·kg$^{-1}$ day$^{-1}$ | FDSE 500 mg.kg$^{-1}$day$^{-1}$ | PTH (30 μg/kg) s.c. injection |
|---|---|---|---|---|
| | BV/TV (%) | 51.62 ± 2.18** | 54.32 ± 2.63** | 60.3 ± 1.91*** |
| | SMI (Index) | 0.8 ± 0.1** | 0.68 ± 0.08** | 0.65 ± 0.07** |
| | Calcein intensity (%) | 11.5 ± 0.88** | 14.88 ± 0.55***## | 15.3 ± .055*** |

*Spinacea* Extract and Butanolic fraction (BF; F004) μCT analysis showing BV/TV, bone volume/tissue volume (%); SMI, structure model index.
Percent Calcein intensityAll values are expressed as mean ± SEM (n = 6 rats/group); *p < 0.05; **p < 0.01 compared to control group. #indicates inter-dose comparison. Formulated Spinacea Extract and formulated butanolic fraction, μCT analysis showing BV/TV, bone volume/tissue volume (%);
SMI, structure model index; All values are expressed as mean ± SEM (n = 6 rats/group); *p < 0.05; **p < 0.01 compared to control group. #indicates inter-dose comparison.

Example 20: Effect of Extract SE on Monosodium Idoacetate Induced Osteoarthritis in SD Rats For induction of MIA-induced arthritis, rats were anesthetized with isoflurane ketamine and xyline 9:1 ratio and given a single intraarticular injection of 3 mg MIA (Sigma) through the infrapatellar ligament of the right knee. MIA was dissolved in physiologic saline and administered in a volume of 50 μl using a gauge, was injection in the left contralateral knee with 50 μl of physiological saline in the other. After OA was induced animals were divided and each group had 6 animals. SE was dissolved in 1.0% gum acacia and was given orally at 250 and 500 mg·kg$^{-1}$day$^{-1}$ doses for 28 days once in a day after the MIA single injection while control group received only gum acacia orally. The effects of SE on microarchitectural deterioration in MIA induced osteoarthritis model were evaluated with microcomputed tomography (SkyScan 1076 scanner; SkyScan, Aartselaar, Belgium). BV/TV, %, Tb.N, mm-1, and Tb.Sp, mm were calculated by the mean intercept length method. Tb.Th, mm was calculated according to the method of Hildebrand and Ruegsegger. Three-dimensional parameters were based on an analysis of a marching cubes Y type model with a rendered surface. At 4 weeks after MIA injection along with 2492 treatment, histological analysis revealed on the subchondral bone fragmented trabeculae of the MIA-treated group, but SE decreased bone loss. Osteophytes were detected in the MIA-treated group, but not in the SE treated groups. Micro-CT analyses showed that treatment with 500 mg·kg$^{-1}$day$^{-1}$ reduced bone and cartilage loss. Damage to the articular cartilage surface was assessed by using India ink at 4 weeks after the MIA injection. Normal joints articular cartilage surfaces of the femoral condyle and the tibial plateau, but the 2492 treatment 250 and 500 mg/kg treated group had smoother articular surfaces than the MIA group. We significantly reduced BV/TV (%)Tb.N), and Tb.Th with significantly increased Tb.Sp compared to control in the MIA group. SE at 250 mg·kg$^{-1}$day$^{-1}$ dose increased BV/TV by 61.12% Tb.Th by 29.5%, Tb.N by 48.51% and decreased in Tb.Sp by 23.9% compared with the MIA group. 500 mg·kg$^{-1}$day$^{-1}$ dose increased the BV/TV by approximately 89.47%, Tb.Th by 50.81%, Tb.N by 76.23% and decreased in Tb.Sp by 21.9%. 500 mg·kg$^{-1}$ day$^{-1}$ doses were more potent in rescuing bone loss. Trabecular response in tibia plateau region, suggested that SE treatment to MIA rats significantly regenerated cartilage and bone-microarchitecture acts as a chondroprotective agent.

Example 21

The pharmacokinetics of butanolic fraction of *Spinacea oleracea* and its formulation were studied after 500 and 250 mg·kg$^{-1}$.d$^{-1}$ respectively. The absorption of both K007 and K008 was rapid with peak serum concentration (Cmax) at 2 h and were monitored up to 8 h on oral administration of formulation. However, the levels were below LLOQ (1 ng/mL) at most of the time points on oral dosing of extract. Because of the insufficient data points the pharmacokinetic parameters could not be generated after oral dosing of extract. The serum concentration-time profile obtained after oral administration of formulation was subjected to non-compartmental analysis and the calculated pharmacokinetic parameters are shown in Table 3. The volume of distribution (K007, 43.3 L/kg; K008, 5.6 L/kg) is larger than the total blood volume of rat (0.054 L/kg; [1]) and systemic clearance (K007, 12.8 L/h/kg) is also higher than the total hepatic blood flow in rats (2.9 L/h/kg; [1]) indicating extravascular distribution along with the extrahepatic elimination.

TABLE 3

Pharmacokinetic parameters of K007 and K008 after oral dosing of 250 mg/kg formulation in male Sprague Dawley rats.

| Parameters | K007 | K008 |
|---|---|---|
| $C_{max}$ (ng/mL) | 7.6 | 5.0 |
| $t_{max}$ (h) | 2 | 2 |
| $AUC_{last}$ (ng h/mL) | 39.0 | 23.3 |
| MRT (h) | 3.4 | 3.9 |
| Cl/F (L/h/kg) | 12.8 | 1.4 |
| $V_{ss}$/F (L/kg) | 43.3 | 5.6 |

Abbreviations:
$AUC_{last}$ = area under the serum concentration-time curve up to last observation,
$C_{max}$ = peak serum concentration,
$t_{max}$ = time to $C_{max}$,
MRT = mean residence

ADVANTAGES OF THE PRESENT INVENTION

The extract of fresh *Spinacia oleracea* has bone anabolic (i.e. new bone formation) effect rather than anti-resorptive (stopping further bone loss) effect of the majority of the anti-osteoporotic agents.

The extract of fresh *Spinacia oleracea* has been found to have rapid fracture healing property with data comparable to standard control PTH.

The major advantage of this invention is that this is comparable to parathyroid hormone (PTH) which is the only anabolic agent but it is expensive and available as injectable. Moreover, it is the last line of therapy given to patients.

The formulated extract presented in this invention is oral obtained from renewable source and is abundant available from natural resource involving no biodiversity issues.

This formulated extract further enhanced bone microarchitecture parameters.

All the compounds exhibited no cytotoxicity on osteoblast cells as cell viability was comparable to the control cells (cells receiving vehicle).

The present study demonstrates that daily oral administration of formulation of phytopreparation (Code 2492/C002) with at favorable doses of 750 mg·kg−1 with fresh *Spinacea oleracea* extract repairs fracture as early as 14 days post fracture. However, at a dose of 750 mg·Kg−1 the formulation group further increased bone volume is to tissue volume (BV/TV) by ~12.9%, Trabecular Number 48.3% (Tb.No.) with decrease in trabecular separation (Tb.Sp.) of ~25.6% and structural model index (SMI) of 52.7% was observed as compared to the non-formulated 750 mg·Kg−1day−1 dose.

Furthermore, the dried *Spinacea oleracea* extract (DSE) was found to repair fracture at a lower dose of 500 mg·kg−1 when compared to either vehicle control group or 750 mg·kg−1 group. In the ovariectomy induced model for osteoporosis in rats fresh *Spinacea oleracea* extract (2492/C002) at 750 and 1000 mg·kg−1 doses mitigates OVx-induced bone loss.

Furthermore, the formulation of dried *Spinacea oleracea* (FDSE) extract was found to repair fracture and regenerate cartilage and improved the osteoarthritis a lower dose of 250 mg·kg−1 which was comparable to positive control PTH. The formulation was found to reduce the dose by 50% when compared to plain Spinach extract (DSE).

The formulation was devoid of any uterine hyperplastic effect, thus raising the possibility of an alternative strategy for the prevention and/or treatment of bone related disorders or osteo-health related disorders including fractures, postmenopausal osteoporosis, mitigation of swelling, inflammation, pain and further in regeneration of cartilage useful in the prevention and/or treatment of osteoarthritis.

We claim:

1. A method of treating or preventing bone fractures, osteoporosis, lost or damaged cartilage, and/or osteoarthritis in a subject in need thereof, comprising: providing an effective amount of a formulation comprising active compounds 5, 3', 4'-trihydroxy-3-methoxy-6,7-methylenedioxy-flavone in a range of 0.01 to 0.07% and 5, 7, 3', 4'-tetrahydroxy-3,6-dimethoxy-flavone in a range of 0.004 to 0.05%, wherein the active compounds are obtained from a spinach extract and/or fraction and provide a bone anabolic effect when administered to the subject.

2. The method of claim 1, wherein the osteoporosis is postmenopausal osteoporosis.

3. The method of claim 1, wherein the formulation comprises one or more of a pharmaceutically acceptable carrier and a pharmaceutically acceptable additive.

4. The method of claim 1, wherein the formulation comprises at least one surfactant/co-surfactant.

5. The method of claim 1, wherein the spinach extract is obtained from *Spinacea oleracea*.

6. The method of claim 1, wherein the spinach extract and/or fraction is obtained using one or more solvents selected from the group consisting of: ethanol, butanol, ethyl acetate, and hexane.

7. The method of claim 1, wherein the formulation utilizes a self-microeinuisifying drug delivery system (SMEDSS).

8. The method of claim 3, wherein the pharmaceutically acceptable carrier is selected from one or more of: oleic acid, castor oil, polyoxyethylene sorbitan monopalmitate, polyoxyethylene sorbitan monostearate, polyoxyethylene sorbitan monooleate, sorbitan monopalmitate, sorbitan monostearate, polyethylene glycol 400, polyethylene glycol 600, propylene glycol and ethanol.

9. The method of claim 3, wherein the pharmaceutically acceptable additive is one or more of: microcrystalline cellulose, polyvinylpyrrolidone (PVP), crospovidone, low-substituted hydroxypropylcellulose, alginic acid, carboxymethylcellulose, calcium salts and sodium salts, fumed silica (colloidal silica), guar gum, magnesium aluminum silicate, methylcellulose, powdery cellulose, starch and sodium alginate.

10. The method of claim 4, wherein the surfactant/co-surfactant is selected from the group consisting of sorbitan esters, polysorbates and polyether compounds.

11. The method of claim 7, wherein the SMEDSS comprises the active compounds in a formulation comprising oleic acid, polyoxyethylene sorbitan monooleate, propylene glycol and polyethylene glycol 600.

12. A method of treating or preventing bone fractures, postmenopausal osteoporosis, damaged cartilage, and/or osteoarthritis in a subject in need thereof, comprising administering a formulation comprising an organic solvent extract of spinach to treat or prevent the bone related disorder, wherein the organic solvent extract comprises 5,3',4'-trihydroxy-3-methoxy-6,7-methylenedioxy-flavone and 5,7,3',4'-tetrahydroxy-3,6-dimethoxy-flavone and is provided at a dose that provides a bone anabolic effect when administered to the subject.

13. The method of claim 12, wherein the organic solvent extract is provided in the formulation at a dose in a range of 25 to 750 mg·kg$^{-1}$·day$^{-1}$.

14. The method of claim 13, wherein the organic solvent extract is provided in the formulation at a dose in a range of 25 to 200 mg·kg$^{-1}$·day$^{-1}$.

15. The method of claim 12, wherein the formulation comprises one or more surfactants/co-surfactants selected from the group consisting of sorbitan esters, polysorbates, and polyether compounds.

16. The method of claim 12, wherein the organic solvent extract is obtained by solvent extraction with a solvent selected from the group consisting of ethanol, butanol, ethyl acetate, and hexane.

17. The method of claim 12, wherein the spinach is *Spinacea oleracea*.

18. The method of claim 12, wherein the organic solvent extract of spinach is formulated with at least one water soluble additive selected from: sodium lauryl sulfate, sodium lauryl ethoxy sulfates, sodium lauryl sulfoacetate, sodium dodecyl benzene sulfonate, alpha olefin sulfonate, ethylene glycols, propylene glycols, sodium lauryl sulfosuccinate, fatty alcohols and fatty alcohol ethoxylates, and nonylphenolethoxylates.

19. The method of claim 12, wherein the formulation utilizes a self-microemulsifying drug delivery system (SMEDSS).

20. The method of claim 19, wherein the SMEDSS comprises the organic solvent extract in a formulation comprising oleic acid, polyoxyethylene sorbitan monooleate, propylene glycol and polyethylene glycol 600.

21. The method of claim 20, wherein the organic solvent extract is dissolved in the SMEDSS in a concentration range of 2.5% to 5% w/w.

* * * * *